(12) United States Patent
Alvi et al.

(10) Patent No.: US 12,380,990 B2
(45) Date of Patent: Aug. 5, 2025

(54) SURGICAL TRACKING AND PROCEDURAL MAP ANALYSIS TOOL

(71) Applicant: DIGITAL SURGERY LIMITED, London (GB)

(72) Inventors: Omar Alvi, London (GB); Andre Chow, London (GB); James Kellerman, London (GB); James Liu, London (GB); Danail Stoyanov, London (GB)

(73) Assignee: DIGITAL SURGERY LIMITED, London (GB)

( * ) Notice: Subject to any disclaimer, the term of this patent is extended or adjusted under 35 U.S.C. 154(b) by 995 days.

(21) Appl. No.: 17/391,137

(22) Filed: Aug. 2, 2021

(65) Prior Publication Data

US 2021/0358599 A1  Nov. 18, 2021

Related U.S. Application Data

(63) Continuation of application No. 16/747,915, filed on Jan. 21, 2020, now Pat. No. 11,081,229, which is a
(Continued)

(51) Int. Cl.
*G06K 9/00* (2022.01)
*A61B 5/00* (2006.01)
(Continued)

(52) U.S. Cl.
CPC ........... *G16H 30/20* (2018.01); *A61B 5/0013* (2013.01); *A61B 34/25* (2016.02); *A61B 90/361* (2016.02);
(Continued)

(58) Field of Classification Search
None
See application file for complete search history.

(56) References Cited

U.S. PATENT DOCUMENTS 8,313,432 B2   11/2012  Chiu et al.
9,307,944 B2    4/2016  Colman et al.
(Continued)

FOREIGN PATENT DOCUMENTS

| DE | 102014003040 A1 | 9/2015 |
|---|---|---|
| WO | 2005084570 A1 | 9/2005 |

OTHER PUBLICATIONS

Darko et al., "LapOntoSPM: an ontology for laparoscopic surgeries and its application to surgical phase recognition", International Journal of Computer Assisted Radiology and Surgery, vol. 10, No. 9, Jun. 11, 2015, pp. 1427-1434.
(Continued)

*Primary Examiner* — S J Park
(74) *Attorney, Agent, or Firm* — CANTOR COLBURN LLP

(57) ABSTRACT

In some embodiments, methods and systems are provided for accessing a surgical dataset including surgical data collected during performance of a surgical procedure. The surgical data can include video data of the surgical procedure. Using the surgical data, a plurality of procedural states associated with the surgical procedure can be determined. For a procedural state of the plurality of procedural states, temporal information can be identified that identifies a part of the video data to be associated with the procedural state. For the procedural state of the plurality of procedural states, electronic data can be generated that characterizes the part of the video data and outputting the electronic data associated with the plurality of procedural states.

17 Claims, 13 Drawing Sheets

Related U.S. Application Data continuation of application No. 15/791,663, filed on Oct. 24, 2017, now Pat. No. 10,572,734, which is a continuation of application No. 15/495,705, filed on Apr. 24, 2017, now Pat. No. 9,836,654.

(60) Provisional application No. 62/464,606, filed on Feb. 28, 2017.

(51) Int. Cl.
| | | |
|---|---|---|
| *A61B 34/00* | (2016.01) | |
| *A61B 90/00* | (2016.01) | |
| *G06V 20/40* | (2022.01) | |
| *G11B 27/34* | (2006.01) | |
| *G16H 15/00* | (2018.01) | |
| *G16H 20/40* | (2018.01) | |
| *G16H 30/20* | (2018.01) | |
| *G16H 70/20* | (2018.01) | |
| *H04L 67/12* | (2022.01) | |
| *H04L 67/561* | (2022.01) | |
| *H04N 5/77* | (2006.01) | |
| *H04N 5/92* | (2006.01) | |
| *A61B 90/50* | (2016.01) | |
| *G16H 40/67* | (2018.01) | |
| *G16H 50/50* | (2018.01) | |

(52) U.S. Cl.
CPC .............. *G06V 20/41* (2022.01); *G06V 20/49* (2022.01); *G11B 27/34* (2013.01); *G16H 15/00* (2018.01); *G16H 20/40* (2018.01); *G16H 70/20* (2018.01); *H04L 67/12* (2013.01); *H04L 67/561* (2022.05); *H04N 5/77* (2013.01); *H04N 5/9201* (2013.01); *A61B 2034/252* (2016.02); *A61B 2034/254* (2016.02); *A61B 2034/256* (2016.02); *A61B 2034/258* (2016.02); *A61B 2090/372* (2016.02); *A61B 2090/373* (2016.02); *A61B 2090/502* (2016.02); *A61B 2560/0487* (2013.01); *A61B 2576/00* (2013.01); *G06V 2201/03* (2022.01); *G06V 2201/10* (2022.01); *G16H 40/67* (2018.01); *G16H 50/50* (2018.01)

(56) References Cited

U.S. PATENT DOCUMENTS

| | | |
|---|---|---|
| 9,788,907 B1 | 10/2017 | Alvi |
| 9,836,654 B1 | 12/2017 | Alvi |
| 9,922,172 B1 | 3/2018 | Alvi |
| 2003/0130973 A1 | 7/2003 | Walton et al. |
| 2007/0136218 A1 | 6/2007 | Bauer et al. |
| 2008/0201280 A1 | 8/2008 | Martin et al. |
| 2009/0089034 A1 | 4/2009 | Penney et al. |
| 2009/0189972 A1 | 7/2009 | Harris et al. |
| 2009/0326336 A1 | 12/2009 | Lemke et al. |
| 2010/0094262 A1 | 4/2010 | Tripathi et al. |
| 2012/0232930 A1 | 9/2012 | Schmidt et al. |
| 2013/0307955 A1 | 11/2013 | Deitz et al. |
| 2014/0267549 A1 | 9/2014 | Pinter et al. |
| 2016/0070436 A1 | 3/2016 | Thomas et al. |
| 2016/0191887 A1 | 6/2016 | Casas |
| 2016/0210411 A1 | 7/2016 | Mentis |
| 2016/0270861 A1* | 9/2016 | Guru .................... G09B 23/28 |
| 2017/0053543 A1* | 2/2017 | Agrawal ................ A61B 90/37 |
| 2017/0084036 A1 | 3/2017 | Pheiffer |
| 2017/0132789 A1 | 5/2017 | Deitz et al. |
| 2018/0247128 A1 | 8/2018 | Alvi et al. |
| 2019/0090969 A1* | 3/2019 | Jarc ...................... A61B 34/10 |
| 2020/0160063 A1 | 5/2020 | Alvi et al. |

OTHER PUBLICATIONS

European Examination Report; Issued: May 25, 2021; Application No. EP 17209562.2; 14 pages.

European Search Report; Issued: Jul. 25, 2018; Application No. EP 17209562.2; 12 pages.

Neumann et al., "Ontology-based surgical process modeling by using SNOMED CT concepts and concept model attributes" 30th International Congress and Exhibition for Computer Assisted Radiology and Surgery, Jun. 20, 2016, 4 pages.

Neumuth, "Surgical Process Modeling—Theory, Methods, and Applications, Habilitation Thesis", Dec. 31, 2012, KP055491527, 279 pages.

Padoy et al., "Statistical modeling and recognition of surgical workflow" Medical Image Analysis 16, 2012, pp. 632-641.

* cited by examiner

SURGICAL TRACKING AND PROCEDURAL MAP ANALYSIS TOOL

CROSS-REFERENCES TO RELATED APPLICATIONS

This application is a continuation of U.S. Nonprovisional application Ser. No. 16/747,915 filed on Jan. 21, 2020, which is a continuation of Ser. No. 15/791,663, filed on Oct. 24, 2017 now U.S. Pat. No. 10,572,734, which is a continuation of U.S. Nonprovisional application Ser. No. 15/495,705, filed on Apr. 24, 2017 now U.S. Pat. No. 9,836,654, which claims the benefit of and the priority to U.S. Provisional Application No. 62/464,606, filed on Feb. 28, 2017. Each of these applications is hereby incorporated by reference in its entirety for all purposes.

FIELD

Methods and systems disclosed herein relate generally to providing procedural guidance data during a surgical procedure. More specifically, procedural guidance data associated with a surgical procedure is represented by a pre-coded surgical procedural map that includes precise and accurate coded descriptions of patient states and surgical actions. Real-time data is processed to identify a particular position within the map, and corresponding procedural guidance data is identified and availed.

BACKGROUND

Variations in procedural methods between different surgeons to accomplish a particular surgical procedure can influence procedural outcomes. Procedural consistency of individual surgeons, in addition to variations in procedural methods, can also influence procedural outcomes. Presently, a number of surgeons achieve procedural outcomes that are below a minimum acceptable level. Further, there are surgeons that achieve outcomes above the minimum but below an average procedural outcome. A tool is needed to help standardize procedural methods between different surgeons and assist individual surgeons with improving procedural consistency.

SUMMARY

In some embodiments, methods and systems are provided for accessing a surgical dataset including surgical data collected during performance of a surgical procedure. The surgical data can include video data of the surgical procedure. Using the surgical data, a plurality of procedural states associated with the surgical procedure can be determined. For a procedural state of the plurality of procedural states, temporal information can be identified that identifies a part of the video data to be associated with the procedural state. For the procedural state of the plurality of procedural states, electronic data can be generated that characterizes the part of the video data and outputting the electronic data associated with the plurality of procedural states.

Some embodiments of the present disclosure include a system including one or more data processors. In some embodiments, the system includes a non-transitory computer readable storage medium containing instructions which when executed on the one or more data processors, cause the one or more data processors to perform part of all of one or more methods and/or part or all of one or more processes disclosed herein. Some embodiments of the present disclosure include a computer-program product tangibly embodied in a non-transitory machine-readable storage medium including instructions configured to cause one or more data processors to perform part of all of one or more methods and/or part or all of one or more processes disclosed herein.

BRIEF DESCRIPTION OF THE DRAWINGS

The present disclosure is described in conjunction with the appended figures.

DETAILED DESCRIPTION

Figure 1:
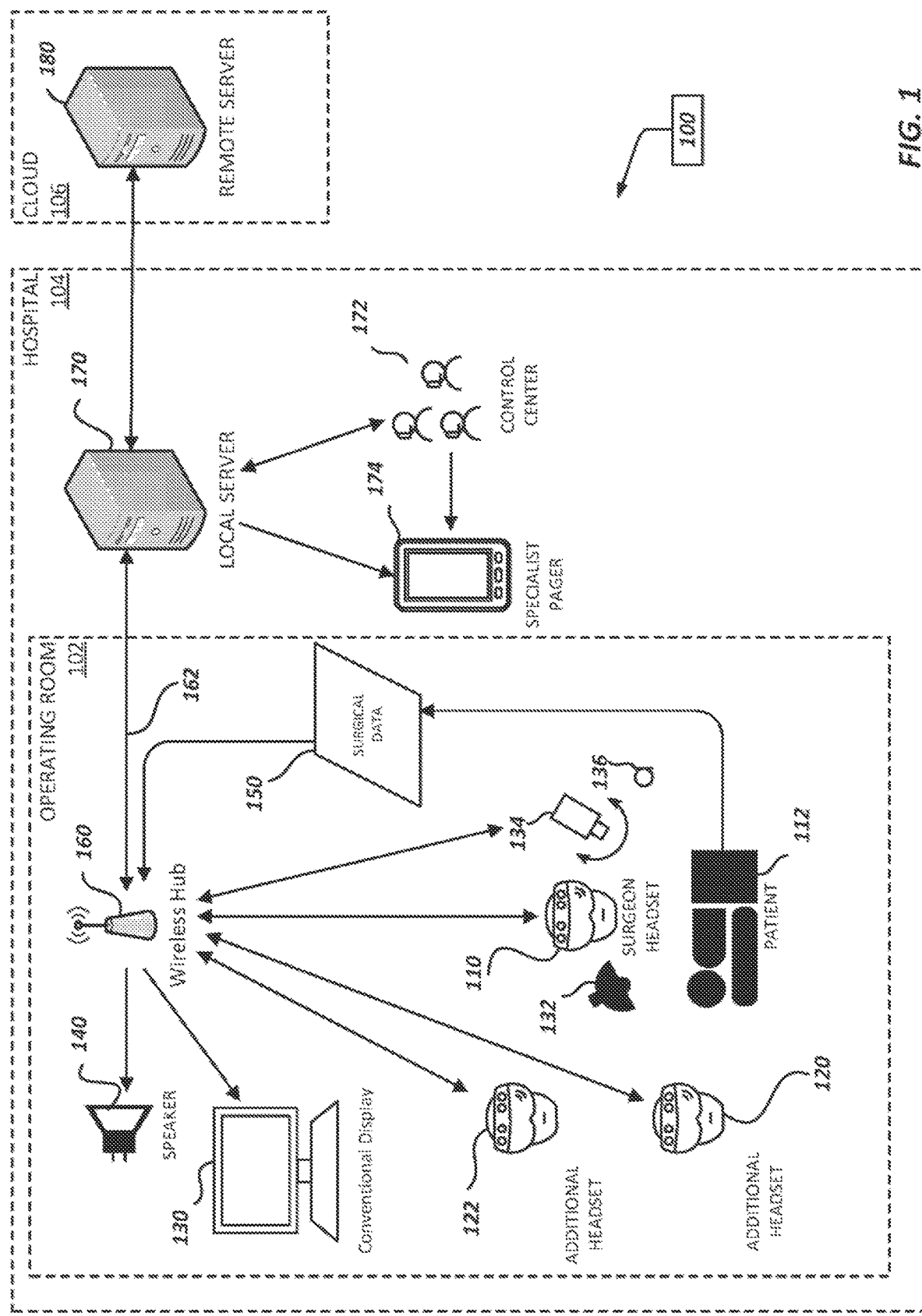
FIG. 1 shows a block diagram of an embodiment of structures and technologies configured to provide surgical guidance using a surgical data structure.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

The structures and technologies described herein may function independently. In some embodiments, the structures and technologies described herein may function in combination to process live data to identify a real-time stage of a surgery, represented in a surgical data structure, which can be used to retrieve or generate pertinent information (e.g., corresponding to a current or subsequent action) for an entire operating room. The structures and technologies described herein may be integrated with existing operating room systems. Further, the structures and technologies described herein may include intelligent system that collects and analyzes operating room data and takes actions that maximize the chances of a desired procedural outcome. Fundamentally, the structures and technologies described herein use a surgical data structure as a reference during live surgical procedures such that appropriate guidance may be provided to the surgeon at the right moment of surgery.

Structures and technologies described herein may describe an appropriate surgical route using the surgical data structure and a number of inputs including one or more user inputs, operating room video or audio streams, smart surgical tools, accelerometer data from a surgeon or other operating room personnel, and patient data. Current textual descriptions of surgery are often verbose, yet semantically constrained by the ambiguity of language they employ. Like GPS navigation relieved users of determining their position using a map or atlas, the structures and technologies described herein relieve surgeons and operating room personnel of tracking patient or procedural states and determining surgery progress from a reference. The structures and technologies described herein determine the procedural location and provide context to operating room personnel for the procedural location and provisions appropriate procedural guidance.

In some embodiments, systems and methods used to process live data to identify a real-time stage of a surgery, represented in a surgical data structure, which can be used to retrieve or generate pertinent information (e.g., corresponding to a current or subsequent action). A surgical data structure, that represents various stage in a surgery and corresponding information, can be locally retrieved or received. During a surgery, live data can be collected (e.g., from a sensor at a wearable device, smart surgical instrument, etc.). The live surgical data can be processed in accordance with the surgical data structure associated with the surgery to identify a specific procedural state (or stage). Procedural metadata associated with the state (e.g., which can include guidance information associated with an anticipated and/or recommended next procedural state) can be retrieved (e.g., from the surgical data structure or from a location identified by the surgical data structure.) and presented.

Accessing the surgical data structure can include (for example) retrieving the data structure from a remote or local data store and/or receiving the data structure from another device (e.g., a cloud server) in response to a request. The surgical data structure may include a plurality of nodes and a plurality of edges. Each edge of the plurality of edges may be configured to connect two nodes of the plurality of nodes. The nodes and edges may be associated with and/or arranged in an order that corresponds to a sequence in which various actions may be performed and/or states may be reached in a surgical procedure. Each of one more or all nodes in the surgical data structure and/or each of one, more or all edges in the surgical data structure may be associated with procedural metadata. The metadata can include description of and/or information corresponding an associated procedural state and/or surgical action. The surgical data structure may include a four dimensional surgical map, three dimensions corresponding to anatomy and the fourth dimension identifying a stage within a procedure.

Live surgical data may be collected by any device integrated with the surgical navigation system. In some embodiments, live surgical data can be collected at a wearable device worn by one or more surgical team members. Live surgical data can also be collected during a surgical procedure via (for example) captured images or video feeds, audio feeds, smart surgical tools, accelerometers on a wearable device on a surgeon, and/or team member inputs. The live surgical data may be encrypted, as necessary, in order to protect the privacy of individually identifiable health information in compliance with the Health Insurance Portability and Accountability Act of 1996.

Third, a processing device may receive the live surgical data. The processing device can be located in or near a surgery location or in the cloud. The processing device can be configured to identify the procedural state and procedural metadata associated with the procedural state. The live surgical data can be processed (e.g., using feature extraction) to identify a state of the patient/surgery. The state of the patient/surgery may be grounded in a physiological state (i.e., the condition or state or the patient's body or bodily functions). In some embodiments, a discrete procedural state (i.e., procedural location and/or procedural action) can be identified based on the state of the patient/surgery and procedural metadata corresponding to a node in the surgical data structure.

Metadata corresponding to the procedural state can be identified. The metadata may be (for example) included in the surgical data structure itself and/or identified by a part of the surgical data structure. For example, a node may include data that identifies surgical tools for an upcoming surgical action or it may point to a location in a table, array, data structure, data store, and so on that may include the particular information. The metadata can be used to generate real-time guidance information for output (e.g., identifying a surgical action to be taken, including an instruction to take a picture for documentation, identifying a tool to be used or prepped, presenting a vital sign for monitoring, paging for assistance, contacting a control center near an operating room with an assistance request, etc.). Guidance information can correspond to decision-tree type of structure. The guidance information may be configured to be presented as text data (e.g., to be presented on a display) and/or non-text data (e.g., audio signals, image overlays, artificial reality data). The type of output (e.g., information presentation versus control-center contact) may differ depending on (for example) a procedural state, patient state or action.

In some embodiments, live surgical data (or a processed version thereof, such as timestamped state identification) can be preserved for a post-hoc analysis. To improve the security corresponding to the live data, the data may be stored so as to anonymize the data and/or to obscure and/or encrypt particular (e.g., private or identifying) features. Live surgical data may be processed to identify current procedural states throughout the surgery. Edges corresponding to actions performed to transition between consecutive states can further be inferred, detected, or identified via an input or other data. Thus, for each surgery, trajectory data can identify a series of actions performed by a surgeon. This data may be aggregated, correlated with surgery outcomes and/or compared to guidance to, for example: (1) assess individual surgeons' compliance with guidelines or requirements; (2) generate audit logs; (3) update recommended actions/edges and/or guidance; and/or (4) identify overall preferences with regard to actions.

Further, live data that includes video content can be used to update a surgical data structure. For instance, a determination that particular frames of video of a surgery corresponds to step 4 of a carpal tunnel procedure can be used to annotate the video. The step identification can indicate what objects should be present in the video (e.g., a patient's hand, a surgeon's hand, and a scalpel blade with a handle masked by 1+ fingers). This knowledge can be used to automatically detect what a scalpel looks like with 1+ fingers covering the handle, which can be used to annotate the video.

Some techniques described herein can improve procedural consistency across entities involved in performance of a surgery (e.g., a surgeon, surgical team, hospital, etc.), improve procedural consistency for a given entity involved in performance of a surgery and/or improve outcomes of a surgery. Further, the real-time feedback can serve to supplement or partly replace training provided by a physically or remotely present procedural expert. Thus, the techniques can promote efficiency in this regard. Additionally, the feedback is provided at a critical time, such that mistakes can be avoided before any harm is cause to a patient.

Referring first to FIG. 1, an embodiment of a system 100 for processing live data to identify a real-time stage of a surgery, represented in a surgical data structure, which can be used to retrieve or generate pertinent information is illustrated. The system 100 can collect live data from a number of sources including (for example) a surgeon mounted headset 110, a first additional headset 120, a second additional headset 122, surgical data 150 associated with a patient 112, an operating room camera 134, an operating room microphone 136, and additional operating room tools not illustrated in FIG. 1. The live data is transmitted to a wireless hub 160 in communication with a local server 170. The local server 170 receives the live data from the wireless hub 160 over a connection 162 and a surgical data structure from a remote server 180. The local server 170 can process the live data to identify a state of the patient/surgery. The local server 170 can identify a node in the surgical data structure corresponding to the discrete procedural state. The local server 170 can process the metadata corresponding to the discrete procedural state and generate real time guidance information for output to the appropriate devices in the operating room 102.

The local server 170 will be in contact with and synced with a remote server 180. In some embodiments the remote server 180 can be located in the cloud 106. In some embodiments processing performed by the local server 170 may be performed by the remote server 180. A global bank of surgical procedures, described using surgical data structures, may be stored at the remote server 180. Therefore, for any given surgical procedure, there is the option of running the system 100 as a local, or cloud based system. The local server 170 can create a surgical dataset that records data collected during the performance of a surgical procedure. The local server 170 can analyze the surgical dataset or forward the surgical dataset to the remote server 180 upon the completion of the procedure for inclusion in a global surgical dataset. In some embodiments, the local server can anonymize the surgical dataset. The proposed system 100 integrates data from the surgical data structure and sorts guidance data appropriately in the operating room using additional components.

In certain embodiments, surgical guidance, retrieved from the surgical data structure, may include more information than necessary to assist the surgeon with situational awareness. The system 100 may determine that the additional operating room information may be more pertinent to other members of the operating room and transmit the information to the appropriate team members. Therefore, in certain embodiments, the complete system 100 provides surgical guidance to more components than the surgeon mounted headset 110.

In the illustrated embodiment, wearable devices such as a first additional headset 120 and a second additional headset 122 are included in the system 100. Other members of the operating room team may benefit from receiving information and surgical guidance derived from the surgical data structure on the wearable devices. For example, a surgical nurse wearing the first additional headset 120 may benefit from guidance related to procedural steps and possible equipment needed for impending steps, see FIG. 6B. An anesthetist wearing the second additional headset 122 may benefit from seeing the patient vital signs in the field of view. In addition, the anesthetist may be the most appropriate user to receive the real-time risk indication as one member of the operating room slightly removed from surgical action.

Distributing the real-time guidance information to team members can avoid work overload of an individual team member. For instance, a surgeon, wearing the surgeon's headset 110, may be overloaded if presented with an equipment list to prepare for the next step in the surgical procedure. Therefore, to distribute workload, the system includes the provision of the first additional headset 120 and the second additional headset 122 to other members of the operating room team. The information presented to the nurse and the anesthetist illustrates how additional information included within the surgical data structure may guide other members of the operating room team besides the surgeon. The additional information and the integration of procedural guidance for operating room team members can benefit the execution of the medical procedure.

In addition to the first additional headset 120 and the second additional headset 122 there may be any number of peripheral information communicating devices including conventional displays 130, transparent displays that may be held between the surgeon and patient, ambient lighting 132, one or more operating room cameras 134, one or more operating room microphones 136, speakers 140 and procedural step notification screens placed outside the operating room to alert entrants of critical steps taking place. These peripheral components can function to provide information that may become critical during the procedure, yet the information displayed does not warrant constant distraction of the surgeon or another member of the operating room team.

Along with these peripheral communication devices, the system 100 can be integrated with any devices within the operating room providing live surgical data 150 concerning the state of the patient 112, for example, heart rate and blood pressure monitors. In addition to vital signs, the live surgical data may include operating room characteristics such as lighting used, ambient temperatures, personnel identification/movement, and any other data that may indicate the progress of a surgical procedure. Sensors that can collect and provide live surgical data 150 may include (for example) electromagnetic sensors, (e.g. hall effect sensors to determine when surgical tools are lifted off an operating room table), optical sensors, in addition to video sensors, and near infrared sensors (to assist with mapping patient anatomy, tracking blood flow, etc.).

This fully integrated operating room system provides a structure through which to automatically coordinate operating room devices with procedural location. The wireless hub 160 may use one or more communications networks to communicate with operating room devices including various wireless protocols, such as IrDA, Bluetooth, Zigbee, Ultra-Wideband, and/or Wi-Fi. In some embodiments, existing operating room devices can be integrated with the system 100. To illustrate, once a specific procedural location is reached automatic functions can be set to prepare or change the state of relevant and appropriate medical devices to assist with impending surgical steps. For example, operating room lighting 132 can be integrated into the system 100 and adjusted based on impending surgical steps.

In another embodiment, in addition to procedural guidance, warnings of hazards can be included within the system. The system 100 may use speaker 140 to warn the operating room of radioactive tracer excretion from the patient 112 and subsequent collection into a suction bag. A visual warning can be presented to operating room personnel using (for example) the surgeon headset 110, the additional headsets, the conventional display 130, and/or operating room lighting 132.

In some embodiments, the system 100 may include a centralized hospital control center 172. This center may be connected to one, more or all active surgeries and coordinate actions in critical situations as a level-headed, but skilled, bystander. In addition to having access to all live data from each operating room (including; video stream, real-time surgical risk, procedural step and other data), a user (e.g., healthcare professional) in the control center 172 may have access to data such as patient records and external personnel availability. In some embodiments, the data available to control center personnel could be packaged and provided as educational material to (for example) medical trainees, residents, and/or students. Control center personnel may have access to the surgical data structure using a surgical data structure explorer. The control center personnel may update the surgical data structure during surgery based on changing patient conditions.

In the event of a surgical complication, the control center manager may be able to directly page the most appropriate specialist on an integrated specialist pager 174 to mitigate the situation. In addition to identifying solutions to critical situations before complications can fully develop, the control center manager has access to information not easily integrated into the system 100 that may be requested by the operating room at times of use. The control center 172 has access to all the data within the operating room 102 and current procedural location, communication between the operating room 102 and control center 172 may take many forms including text communications and direct audio or visual links.

In some embodiments, a risk indication can be displayed within the system 100 to inform the progression and seriousness of surgery. To minimize distraction or stress, the system 100 may display the risk solely to a member of the operating room team removed from the present step of the surgery using (for example) the first additional headset 120 or the second additional headset 122.

In certain embodiments, the indication of real-time surgical risk can be used to inform the operating room team of the risk or to trigger complication avoidance methods by the system. For example, when the risk reaches a pre-defined threshold or a level computed in real-time, the system may provide additional guidance directly to the surgeon using the surgeon headset 110, an alert communication can be transmitted a local hospital control center 172 so the situation can be monitored more closely, and/or a relevant specialist pager 174 can be activated to contact a specialist necessary to resolve the situation. The risk level computed in real-time may be based on the surgical map and/or the probability of achieving optimal outcomes. In some embodiments, the system may dynamically flag an alert for procedural states, actions, or any other points in the surgical map.

In some embodiments, the system 100 calculates real-time surgical risk. The response of the system 100 based on this real-time risk can be flexible. The response may be adjusted by (for example) each hospital 104 or control center 172. For example, the defined risk threshold upon which responses are actioned may be changed, or the individual parameter weighting for calculating risk may be manipulated. A user (e.g., surgeon, nurse or team member) may access the surgical data structure pre-surgery in the control center 172 using a surgical data structure explorer. The user may customize the risk thresholds or individual parameter weightings based on (for example) surgeon, team member, patient, and/or hospital specific characteristics.

The system 100 may adjust response actions based on other information, such as a surgeon's level of skill. The surgical data structure may include a variable corresponding to a surgeon's level of skill (e.g., corresponding to a particular occupational position, duration at a particular facility, duration practicing surgeries generally or of a particular type, complication probability based on past surgeries, and so on). The system 100 may determine the value for the variable corresponding to the surgeon's level of skill by analyzing pre-recorded surgical data associated with a surgeon or the variable may be entered by a user (e.g., surgeon, nurse or team member). For example, a trainee surgeon may have a lower threshold of risk before actions or insistent warnings are issued, a more experienced consultant may have to reach a higher level of risk before the same actions are issued. Using a tiered risk management system, the system 100 may reduce unnecessary risk by providing guidance to a user (e.g., surgeon, nurse or team member) and notifying specialists at the appropriate times. Reducing the unnecessary risk may decrease the occurrence of unfavorable patient outcomes.

A system 100 is not limited to the embodiments illustrated in FIG. 1. Some embodiments of a system 100 may remain the same with significant change in component organization. The embodiments herein relate to the provision of an intelligent system, which integrates with the whole operating room team, operating room data and procedural guidance; the embodiments herein do not relate to a specific medical device network structure.

Figure 2:
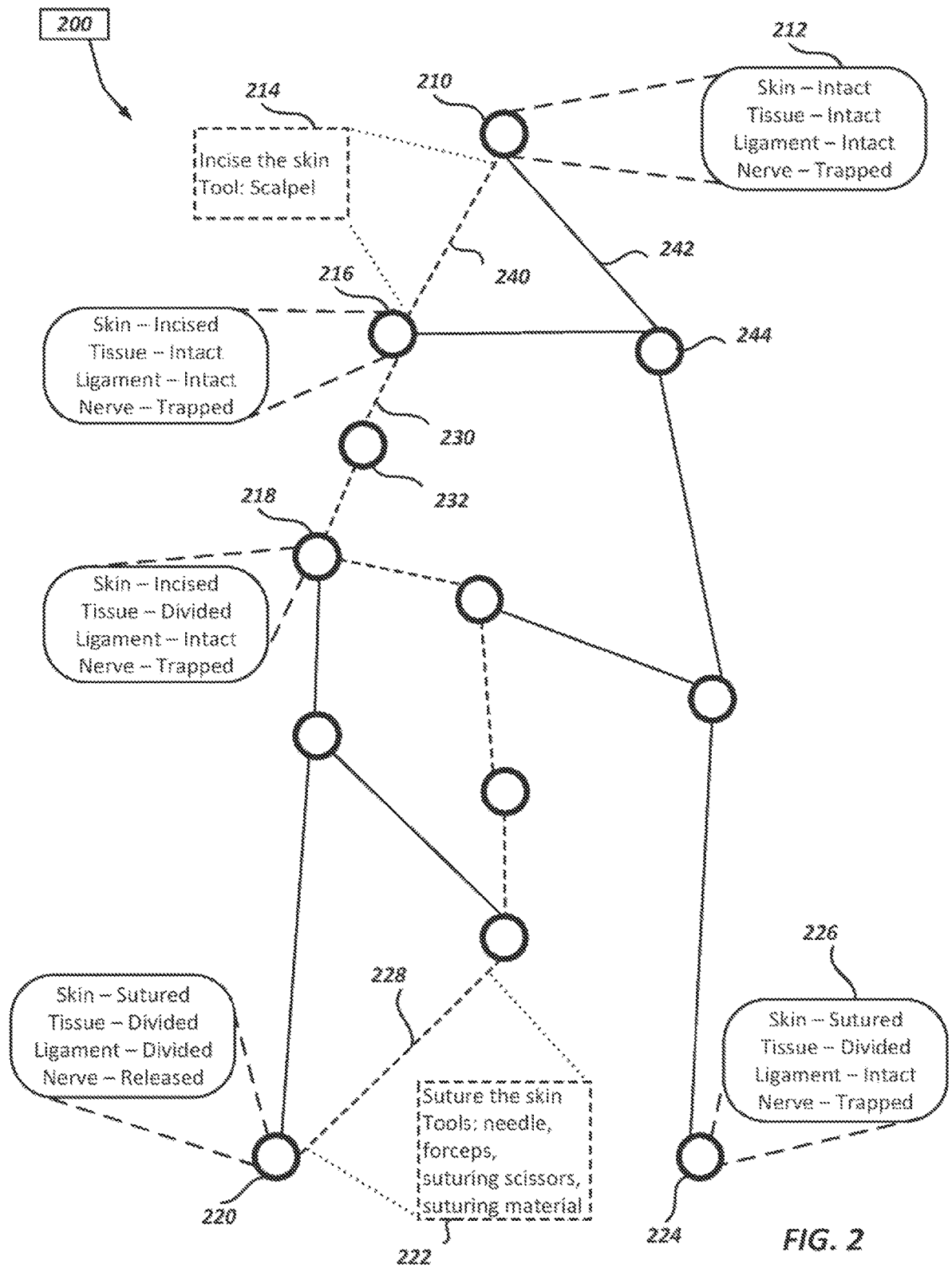
FIG. 2 shows an embodiment of a surgical data structure.

Referring next to FIG. 2, one possible embodiment of a surgical data structure 200 is shown. In some implementations, the system for processing live data to identify a real-time stage of a surgery, which can be used to retrieve or generate pertinent information, is grounded on a surgical data structure 200. The surgical data structure 200 allows concise descriptions of complex medical procedures. A discrete route through a surgical data structure 200 embodies a codified description of a specific surgical procedure. The surgical data structure 200 may include the information needed for the reproduction of an individual procedure and additional information to describe both subtly different and alternative procedural methods between individual users (e.g., surgeon, nurse or team member), yet, no more information than necessary to achieve both objectives.

In some embodiments, the precise route taken through a surgery is characterized by a series of transitions between discrete patient states. The surgical data structure 200 may describe medical procedures in full using graph theory or network structures. Within this graphical notation, a node 210 can represent a discrete physiological and procedural state of the patient during a procedure (e.g., initial preparation and sterilization complete, skin incision made, bone exposed, etc.). The node 210 may represent a pose, anatomical state, sterility, etc. The node 210 can be grounded in a 3D anatomical state. A 3D anatomical state characterizes a state of a patient, such as patient position, location of an organ, location of a surgical instrument, location of an incision, etc.

The node 210 and the associated discrete procedural state can be associated with a set of procedural metadata 212 that can include (for example) a description of and/or information corresponding to a procedural state. Procedural metadata 212 associated with a node 210 can include, for example, a description of a surgical action to be taken, an instruction to take a picture for documentation, a description of a surgical tool to be used or prepped, a description of a vital sign for monitoring; and/or a recommendation to page a control center for assistance. In some embodiments, the procedural metadata 212 can include a decision tree in machine readable format for use by a processing device or in natural language form for use by one or more system users.

Figure 3:
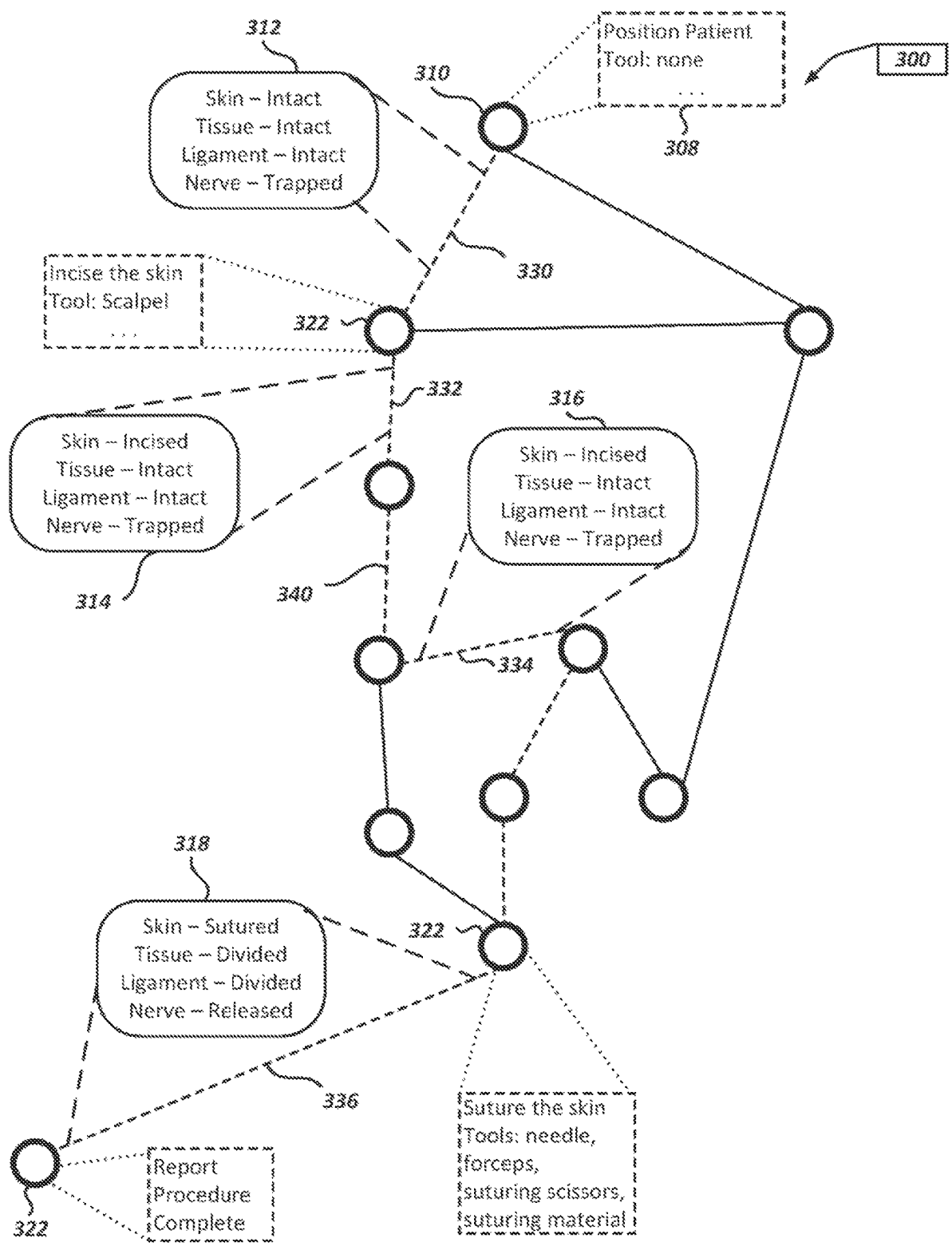
FIG. 3 shows an alternate embodiment of a surgical data structure.

An edge 240 can represent one or more surgical actions executed to transition between different nodes. In other embodiments, as shown in FIG. 3 and described further below, edges may represent distinct states of the patient during a procedure and nodes may represent surgical actions taken to transition between different edges. Each edge may represent a medical action to be performed that will result in a transition between states. Each edge can be associated with information about the surgical action, such as an identification of the action, a time typically associated with the action, tools used for the action, a position of interactions relative to anatomy, etc.

In some implementations, for each individual procedure, the surgical data structure 200 is a multidimensional space representing the many routes that a single procedure may take. A single route through this multidimensional map may represent one method of executing the surgical procedure. The surgical data structure 200 may include a plurality of routes through the multidimensional map, including a preferred route 230, indicated by a dashed line. The preferred route 230 may be linked to a number of factors including (for example) user (e.g., surgeon, nurse or team member) experience, operating room equipment, operating room personnel, minimizing risk, and/or surgical outcomes. The surgical data structure 200 allows the precise definition of important surgical landmarks using a constrained coded vocabulary.

Each node 210 may be associated with a set of procedural metadata 212 that can include a description of and/or information corresponding to the discrete procedural state. The description of and/or information corresponding to the discrete procedural state includes many different attributes that describe the condition of a patient at a given point during a medical procedure. The attributes describing patient state may include, but are certainly not limited to pose, anatomical state, and sterility. Any number of attributes may be needed in order to ensure a node is accurately described, and this may vary for different surgical procedures. The attributes associated with a discrete procedural state may also include variables not related directly to the patient but to the surgical procedure. For example, the personnel present in the operating room may relate to the state of the surgery but not to any particular patient state. In some embodiments, the fewest number of attributes is desirable. The description of and/or information corresponding to a discrete procedural state may describe a procedural state with sufficient detail to be used by a processing device in a feature extraction algorithm.

In some embodiments, each of one, more or all nodes is grounded in a 3D anatomical state (e.g., characterizing a state of a patient, such as a position, location of an organ, location of a surgical instrument, location of an incision, and so on). As such, the node 210 may include a detailed description of anatomical state. Surgical interventions aim to modify anatomy and their progress is constrained by patient topology. Thus, anatomical state and organization may present important checkpoints to split a complex procedure into discrete steps. These steps must be passed, regardless of method or prior event sequence. For example, to perform a total knee replacement, the skin must be cut and the bones at the knee joint exposed in order for the replacement knee to be applied.

In certain embodiments, using a surgical data structure 200 based on a graph model of surgery, edges 240 describe the transition between different nodes—each node representing a different patient state. As such, edges 240 represent actions taken by the users (e.g., surgeon, nurse or team member) during the procedure. Each edge may be associated with action specific metadata 214, including, but not limited to: time taken, tools used, state of the tools used, and position of interactions relative to anatomy. In other embodiments, nodes may represent actions taken by the users (e.g., surgeon, nurse or team member) during the procedure and edges may provide a description of the patient state.

Node-to-node transitions in surgery may take multiple different routes between the same two destinations depending on factors entirely distinct from the two nodes. In some implementations, node-aware systems and methods facilitate flexible routes between a single destination node. Furthermore, different node-to-node transitions (i.e., surgical actions), or entirely different routes through the surgical data structure 200, may be recommended for different age patients in the same procedure.

In some embodiments, for the provision of the structures and technologies described herein, the surgical data structure 200 must be translated from a generic coded anatomical model to real anatomy. For example, the surgical data structure 200 may need to be anatomically adjusted for success in specific procedures. Some embodiments may adjust the surgical data structure 200 for obese patients, patients with atypical anatomy or patients who may have undergone significant surgical procedures in the past.

The surgical data structure 200 may include anatomical models that are both malleable and include topologies that can be expected to remain consistent between many different patients. In some embodiments, the surgical data structure 200 may account for the anatomical distinction between the sexes, which may impact the description of certain surgeries. In certain embodiments, a selection of patient specific anatomic models may need to be implemented, or existing models adjusted in certain situations.

To further illustrate the use of a surgical data structure 200, an embodiment describing a subset of steps performed during the surgical procedure for carpal tunnel release is provided herein. Carpal tunnel release surgery is a simple procedure to relieve the symptoms of carpal tunnel syndrome. The carpel tunnel is a narrow passage within the wrist capped by the carpal ligament. The syndrome is caused when the median nerve becomes compressed, often by swelling, within the carpal tunnel. The crucial step of carpal tunnel release surgery is to cut this ligament to release the median nerve and alleviate the symptoms of carpal tunnel syndrome. Above the ligament is a layer of tissue and a layer of skin respectively. Both must be divided in order to reach the carpal ligament.

FIG. 2 details a simplified representation of a surgical data structure 200 for a carpal tunnel release procedure. To accomplish the carpal tunnel release procedure, at least four crucial procedural nodes 210, 216, 218, and 220 may be defined by the anatomic states of four relevant pieces of anatomy: the skin, wrist tissue, carpal ligament and median nerve. Representative procedural metadata 212 is provided for each of the four crucial procedural nodes 210, 216, 218, and 220. During the carpal tunnel release procedure the skin, tissue and ligament may be intact or divided and the nerve trapped or released. The procedural metadata 212 may include additional data not illustrated in FIG. 2. The additional data may include attributes used to define more nodes along the route of surgery (such as the sterility of the surgical site), but these four anatomical states represent nodes through which the procedure must pass to progress.

The four key procedural nodes 210, 216, 218, and 220 are connected by edges, which represent surgical interactions related to the associated node-to-node transition. For example, edge 240 may represent the action necessary to transition from the first key procedural node 210 to the second key procedural node 216. The procedural metadata associated with the second key procedural node 216 indicates that the skin is incised. In order to facilitate the transition between procedural states, edge 240 represents the procedural action associated with the node-to-node transition. In this example, the action specific metadata 214 associated with edge 240 includes a description of the action, "incise the skin," and the tools required, "scalpel." The procedural action associated with edge 240 causes the associated physiological state of the skin to transition from intact to incised between node 210 and node 216 respectively.

The four key procedural nodes 210, 216, 218, and 220 are illustrated on the preferred route 230. The preferred route 230 passes through an intermediate node 232 to the third key procedural state 218. The set of procedural metadata associated with the third procedural state 218 indicates that the tissue above the ligament has been divided. The final key procedural node 220 is associated with procedural metadata that indicates that the nerve has been released and the surgical preferred route 230 has reached a successful surgical outcome. The preferred route includes a final edge 228 that includes an instruction to "suture the skin" and a set of tools required to complete the procedural action.

In some embodiments, the surgical data structure 200 can account for surgical procedures that do not reach a procedural state associated with a successful surgical outcome. FIG. 2 shows unsuccessful node 224 and its associated unsuccessful metadata 226 indicating that the nerve is still trapped after traversing the nodes in the surgical data structure 200.

For simplicity, the complete list of possible attributes associated with the metadata for each node and edge has not been included in this stylized representation. A longer list of possible attributes may include, (for example) surface sterility, the interaction with specific instruments or physical characteristics such as the pressure or tension on specific anatomical structures, and/or patient vital signs.

To simplify the surgical data structure 200 of this surgery further, the route may be represented as distinct nodes without any metadata 244. The four key procedural nodes 210, 216, 218, and 220 and relevant edges shown in FIG. 2 are only a small subsection (individual surgical route) of a large, multidimensional surgical data structure including many possible nodes and edges. A surgical data structure may represent all projected surgical paths possible within the procedure.

In some embodiments, nodes and edges may be defined as a list of contingent events. For example, the retraction of the skin is contingent on its initial incision. By defining each set of data (i.e., a node or an edge) in contingent terms, the network is able to self-construct, by forming all possible actions given the extended rules of contingency. In certain embodiments, the structures and technologies described herein may capture live surgical data to build descriptions of procedures, coded in the structure defined above. In some examples, the the structures and technologies described herein may harvest nodes and edges directly from surgical procedures themselves and construct a surgical data structure automatically.

In other embodiments, different successful routes may interconnect. FIG. 2, illustrates that more than one route in the surgical data structure 200 is possible. In certain embodiments, the preferred route 230 refers to a set of successful procedural routes which constitute a very small subsection of a much larger, multidimensional surgical data structure, where each node and edge are can include a description of and/or information corresponding to surgical states and actions respectively. In certain embodiments, there may be more than one successful procedural route. Graph theory concepts can then be applied to facilitate provision of real-time guidance (e.g., identifying one or more edges to cause a transition between two nodes defined for a surgery) or to facilitate post-hoc data analysis of one or more surgeries (e.g., to identify which paths are associated with particular consequences, an extent to which a predefined procedure was followed, etc.).

FIG. 3 illustrates an embodiment of the surgical data structure 300 where surgical actions are associated with nodes 310 and procedural states are associated with edges 330. FIG. 3 uses the carpal tunnel procedure to illustrate an alternate embodiment of a surgical map. FIG. 3 illustrates the four key procedural states associated with edges 330, 332, 334, and 336. Each key procedural state includes metadata to provide a description of and/or information corresponding to the procedural state.

In the embodiment illustrated by FIG. 3, the first node 310 is associated with a procedural action. The action metadata 308 includes instructions and tools necessary to perform the procedural action. The first node 310 includes instructions to position the patient. The first key procedural state is associated with a first edge 330. The first edge 330 is associated with a set of procedural metadata 312 and includes a description of and/or information corresponding to the first key procedural state. The preferred route 340, shown by the dashed line in FIG. 3, connects each of the four key procedural states. A second edge 332 is associated with a second set of procedural metadata 314 indicating physiological states associated with the second key procedural state. A third edge 334 is associated with a third set of procedural metadata 316 indicating physiological states associated with the third key procedural state. A fourth edge 336 is associated with a fourth set of procedural metadata 318 indicating physiological states associated with the fourth and final key procedural state. A plurality of nodes 322 are associated with procedural actions and action metadata connect the key procedural states associated with edges 330, 332, 334, and 336

Figure 4:
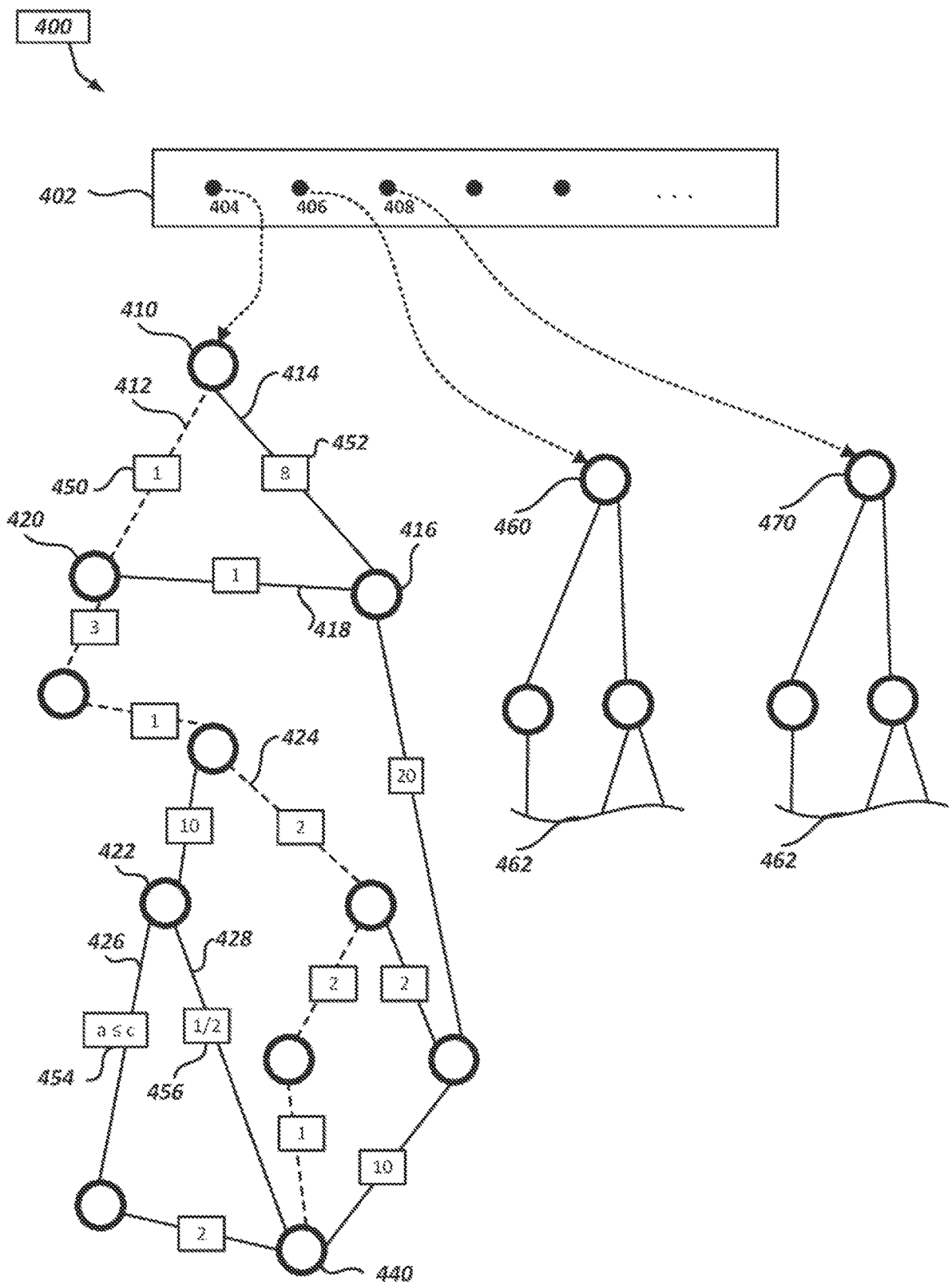
FIG. 4 shows relation of multiple surgical data structures.

FIG. 4 illustrates a surgical data structure 400 that can recommend a preferred surgical route 424 based on weights assigned to one or more edges between the node-to-node transitions. In some embodiments, a weight may be assigned to each node in addition to, or in lieu of, the weight assigned to each edge. The weights may be associated with a plurality of factors including, (for example) surgical outcomes, risk, prevalence of use, current procedural state, patient characteristics, vital signs, procedure specific parameters, and/or user (e.g., surgeon, nurse or team member) experience. The risk may be based on maximum risk or a risk based on the probability of occurrence. The weights may be manually assigned when constructing the surgical data structure. In other embodiments, the surgical weights may be determined or updated using a machine learning algorithm based on collected surgical data, including surgical outcomes. In some embodiments, a user (e.g., surgeon, nurse or team member) may update the weights pre-surgery using a surgical data structure explorer.

The weight 450 assigned to an edge 412 may be based on a number of factors. In some embodiments, the weight 450 may be associated with the probability of a transition from a first node to a second node. In FIG. 4, the weight 450 is assigned to a first edge 412 and a second weight 452 is assigned to a second edge 414. In this example, the weight 450 is lower than the second weight 452 and the lower weight may be associated with a preferred edge. The second weight 452 may be higher because in order to arrive at a preferred node 420, a surgeon must perform two surgical actions and pass through an intermediate node 416. In selecting the second edge 414, the surgeon performs a surgical action associated with the second edge 414 to reach intermediate node 416. Next, the surgeon must complete the surgical action associated with intermediate edge 418 to arrive at the preferred node 420.

In some embodiments the systems and methods described herein can use the weights assigned to the edges of the surgical data structure to determine a preferred route 424, illustrated as a dashed line in FIG. 4. The preferred route 424 may be determined by adding the weights of the connected edges to calculate a cost of traversing from an initial node 410 in the surgical data structure to a destination node 440 in the surgical data structure. In other embodiments, the preferred route may be recalculated using a current node and a target node that are a subset of nodes in the surgical data structure. The target node can be a node in the surgical data structure selected by (for example) a surgeon, an operating room team member, control room personnel, and/or one or more automated methods described herein.

The systems and methods described herein may calculate a cost for a route in the surgical data structure. Determining the cost may depend on whether weights are included in the surgical data structure. The cost may be calculated based on how values are assigned to the weights in the surgical data structure. In some embodiments, the lowest cost route may be the route selected. In other embodiments, the cost may be just one input into a processor that is configured to determine a route from an initial node to a destination node.

In other embodiments, the weights associated with the edges of a surgical data structure may be associated with an actual value and a maximum value. Weight 454 illustrates that edge 426 may be selected if actual value 'a' is less than the capacity 'c'. In some embodiments, the capacity may represent patient vital signs. Edge 428 may be associated with a surgical action that may be performed if a set of vital signs are below a set of threshold values. Vital sign weight 456 can represent that edge 428 is available for selection if less than or equal to '2' vital signs are below threshold values. For example, the '1' in vital sign weight 456 can indicate that the patient's heart rate is above a threshold value but blood pressure and breathing rate are at acceptable levels. As a result, edge 428 is available for selection to transition from a present node 422 to a destination node 440.

In some embodiments, the structures and technologies described herein include a global surgical graph 402 that may include a map to a plurality of pre-coded surgical data structures. During a surgical procedure using a fully developed pre-coded surgical data structure, there is a very low probability of a surgical complication that may cause a patient to transition to a procedural state that is not associated with a node. For example, the first pre-coded surgical data structure 404 may start at node 410 and represent the carpal tunnel procedure discussed above. Some rare carpal tunnel complications that may still need to be accounted for include heart attacks and pulmonary aspiration. During the carpal tunnel procedure, the patient may transition to a procedural state associated with a complication that is not represented by a node in the first pre-coded surgical data structure 404.

To account for low probability complications, the systems and methods described herein may transition to another pre-coded surgical data structure in the global surgical graph 402. For example, during the carpal tunnel procedure, the global surgical graph 402 can include a second pre-coded surgical data structure 406 associated with treating a patient experiencing a heart attack, and a third pre-coded surgical data structure 408 associated with treating a patient experiencing aspiration. The second pre-coded surgical data structure 406 begins at node 460, which includes a description of and/or information corresponding to a procedural state and patient attributes associated with a heart attack. The third pre-coded surgical data structure 408 begins at node 470, which includes a description of and/or information corresponding to a procedural state and patient attributes associated with pulmonary aspiration. The second pre-coded surgical data structure 406 and the third pre-coded surgical data structure 408 continue beyond line 462 to a node associated with a desired outcome for each procedure.

In some embodiments, the systems and methods described herein may automatically transition between the surgical data structures included in the global surgical graph 402. In addition to the automatic transition, the systems and methods described herein may automatically transmit an alert to a specialist to assist with the associated complication. In alternate embodiments, the control center may monitor surgical data and determine that the current procedural state is not associated with a node in the present surgical data structure. The control center may select an appropriate surgical data structure to transition to based, for example, on the procedural state, surgical data, and/or other factors related to the patient state. The control center may page a specialist based on the severity of the complication.

In certain embodiments, the surgical data structure may be customized to direct surgery using the structures and technologies described herein. For example, a user (e.g., surgeon, nurse or team member) may access a surgical data structure prior to surgery and manually select any acceptable procedural route before surgical navigation is initiated. Furthermore, the whole procedure may be specifically planned, such that a tailored route (where a user chooses every node and edge) can be defined before the procedure. The structures and technologies described herein may provide a user (e.g., surgeon, nurse or team member) the capability to edit a surgical data structure using a software application such as a surgical data structure explorer. In alternate embodiments, the structures and technologies described herein may be configured to recommend the most appropriate surgical route, dependent on patient specific data (e.g., and/or live data). Further, the weights associated with the surgical data structure may be specifically set by the systems and methods described herein or by a user (e.g., surgeon, nurse or team member) before a specific surgical procedure.

In some embodiments, machine learning may be used to identify an action to recommend in a given circumstance (e.g., current state, patient characteristic, vital sign) and/or to a given operating room team member. Action recommendation may be based on assessing potential and/or expected risk associated with each of one or more actions. For example, a potential risk may be defined as a maximum risk impact or a weighted sum of risk impact (weighted based on probability of occurrence), and a selection may then be made to select an action with a lowest, low or below-threshold risk impact.

Figure 5:
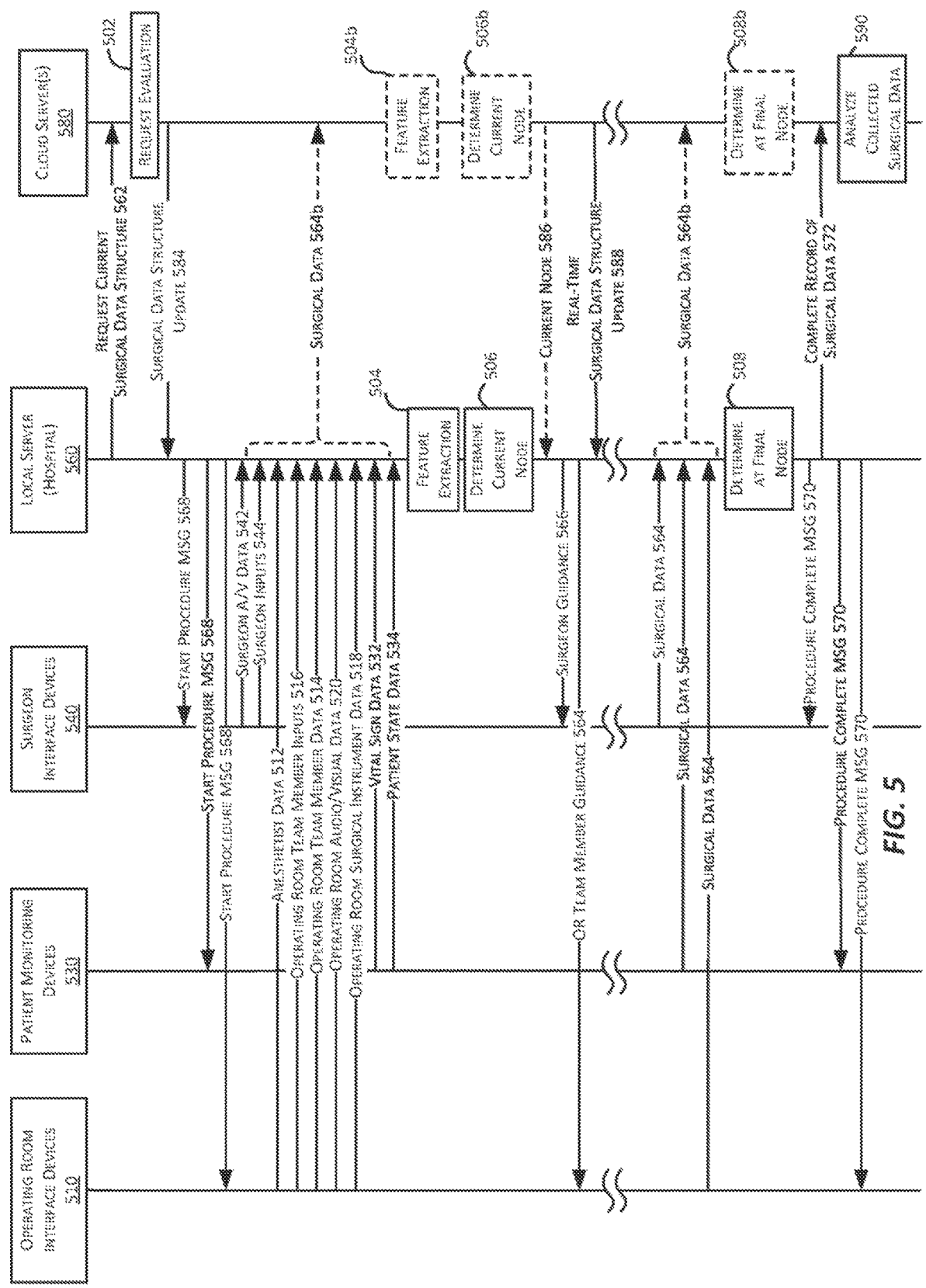
FIG. 5 shows an embodiment of the data flow in the structures and technologies configured to provide surgical guidance using a surgical data structure.

FIG. 5 provides a schematic illustration of communication exchanges between the structures and technologies described herein. The structures and technologies described herein includes operating room interface devices 510, patient data devices 530, surgeon interface devices 540, local server 560, and cloud server 580. The operating room interface devices 510 can include operating room cameras and microphones, non-surgeon operating room team member headsets, smart surgical tools, power usage, light source usage, suction devices, irrigation devices. The patient data devices 530 can include any patient monitoring equipment including vital signs, patient discharge measuring devices, and ventilation volume measurements. Surgeon interface devices 540 can include an interface device, such as a headset and additional surgeon monitoring devices. Additional surgeon monitoring devices may include galvanic skin response devices and accelerometers to determine surgeon stress levels. As illustrated, the local server 560 may generate and transmit a request for the current surgical data structure 562 from the cloud server 580. The request may include version information including a version number, a date, or other indication of the local server version of the surgical data structure.

The cloud server 580 will perform a request evaluation 502 to determine if the local server 560 has the current version of the surgical data structure. In performing the request evaluation 502, the cloud server will determine whether the local server 560 has the current surgical data structure. After evaluating the request, the cloud server 580 will generate and transmit a surgical data structure update 584 to the local server 560. If the local server has the current version of the surgical data structure, the contents of the surgical data structure update 584 will be limited. If the surgical data structure is not current, the surgical data structure update 584 will include updates for the associated surgical data structure. In some embodiments, the request for the current surgical data structure 562 may be associated with a surgical data structure not present on the local server 560. In this case, an entire surgical data structure may be included in the surgical data structure update 584.

Upon receiving the surgical data structure update 584 the local server 560 may generate and transmit a start procedure message 568 to the surgeon interface devices, the patient data devices, and the operating room interface devices. The start procedure message 568 may include machine readable instructions that instruct the devices to begin collecting surgical data associated with the surgical procedure. Each device may generate and transmit surgical data to the local server.

Upon receipt of the start procedure message 568, the surgeon interface devices 540 and the operating room interface devices 510 will present relevant procedural information to the surgeon and the operating room personnel respectively. Additionally, upon receipt of the start procedure message 568, the surgeon interface devices 540, the patient data devices 530, and the operating room interface devices 510 will begin recording and transmitting data to the local server 560. The data recorded and transmitted by the surgeon interface devices 540, the patient data devices 530, and the operating room interface devices 510 may be categorized as surgical data 564.

Specific surgical data is generated by each of the devices in the structures and technologies described herein. The surgeon interface devices 540 generate audio and/or visual data (A/V data) associated with the surgeon's actions. The surgeon interface device 540 may be configured to receive inputs from a surgeon. Inputs may be auditory, visual, or haptic. In some embodiments, the surgeon's inputs may be in response to a stimulus. The surgeon A/V data 542 and the surgeon inputs 544 are transmitted to the local server 560. The patient data devices 530 generate and transmit vital sign data 532 and patient state data 534 to the local server 560. Data associated with operating room interface devices 510 includes anesthetist data 512, operating room team member inputs 516, operating room team member data 514, operating room visual data 520, and operating room surgical instrument data 518. The data associated with operating room interface devices 510 is also transmitted to local hospital server 560.

Next, the local server 560 performs feature extraction 504 and determines a current node 506. Feature extraction 504 is performed by the local server 560 using the surgical data 564 generated and transmitted by the operating room interface devices 510, the patient data devices 530, and the surgeon interface devices 540. The local server 560 may detect components related to the procedural metadata stored in the surgical data structure using feature extraction 504. For example, components may include anatomical states, phonemes, and/or surgical tools. In some embodiments, the feature extraction 504 can include extracting visual or auditory components from the live surgical data.

Local server 560 determines a current node 506 using the surgical data structure and the components extracted from the surgical data 564. In an alternate embodiment, the local server 560 forwards surgical data 564$b$ to the cloud server 580. The cloud server may perform feature extraction 504$b$, determine a current node 506$b$, and transmit the current node 596 to local server 560.

Based on the current node the local server 560 generates and transmits surgeon guidance 566, and OR team member guidance 564. The guidance may include information from the metadata associated with the current node and/or information related to a procedural action associated with an edge to transition from the current node to a target node. In some embodiments, the surgical data structure (or a version thereof) may be updated (e.g., at the cloud server 580 or at the local server 560) during a surgical procedure or at another time. For example, the update may be based on the surgical data 564$b$ received at the cloud server 580. The cloud server 580 may generate and transmit a surgical data structure update 588 to the local server 560 during the surgical procedure. The Operating room interface devices 510, patient monitoring devices 530, and surgeon interface devices 540 continue generating and transmitting surgical data, and the local server 560 continues extracting features and determining current nodes until the local server 560 determines the surgical procedure is at a final node 508. In some implementations, the local server 560 may transmit surgical data 564$b$ to the cloud server 580, which determines the surgical procedure is at a final node 508$b$.

Upon determining the surgical procedure is complete, the local server 560 may transmit a procedure complete message 570 to the operating room interface devices 510, the patient data devices 530, and the surgeon interface devices 540. In response, the devices may present information to operating room team members and the surgeon that indicate the surgical procedure is complete. Further, the devices may stop transmitting surgical data to the local server upon receiving the procedure complete message 570. In some implementations, the local server 560 may transmit a complete record of the surgical data 572 associated with the surgical procedure to the cloud server for analysis.

After receiving the complete record of surgical data 572, the cloud server may analyze collected surgical data 590. Analyzing the collected surgical data may include determining updates to the surgical data structure, determining user (e.g., surgeon, nurse or team member) compliance with procedure guidelines, and annotating the record of surgical data to indicate data associated with procedural states. Updates to the surgical data structure may include (for example) updating the metadata associated with current nodes and edges, generating new nodes, generating new edges to transition between current nodes and new nodes, updating the weights associated with edges, and/or deleting nodes/edges no longer present in a surgical procedure.

In some embodiments, analyzing the collected surgical data may include generating an annotated video file that includes video data and annotations associated with the nodes and edges present in the video data. In other embodiments, analyzing the collected surgical data may include generating compliance data that identifies entities involved in the surgical procedure and any departures from the preferred surgical guidelines. The compliance data may be stored in a compliance dataset. The compliance dataset can be transmitted to (for example) the surgeons that performed the procedure, medical schools, and/or medical review boards.

In some embodiments, analyzing the collected surgical data may include integrating the present set of surgical data with a global set of surgical data. The remote server can be configured to process the global set of surgical data and apply machine learning techniques to update the surgical data structure based on the global surgical data. For example, the global surgical dataset may contain distinct features and components that are not linked with a node in the associated surgical data structure. In response, the remote server may define a new discrete procedural state and update the associated surgical data structure with the appropriate nodes and edges.

Figure 6A:
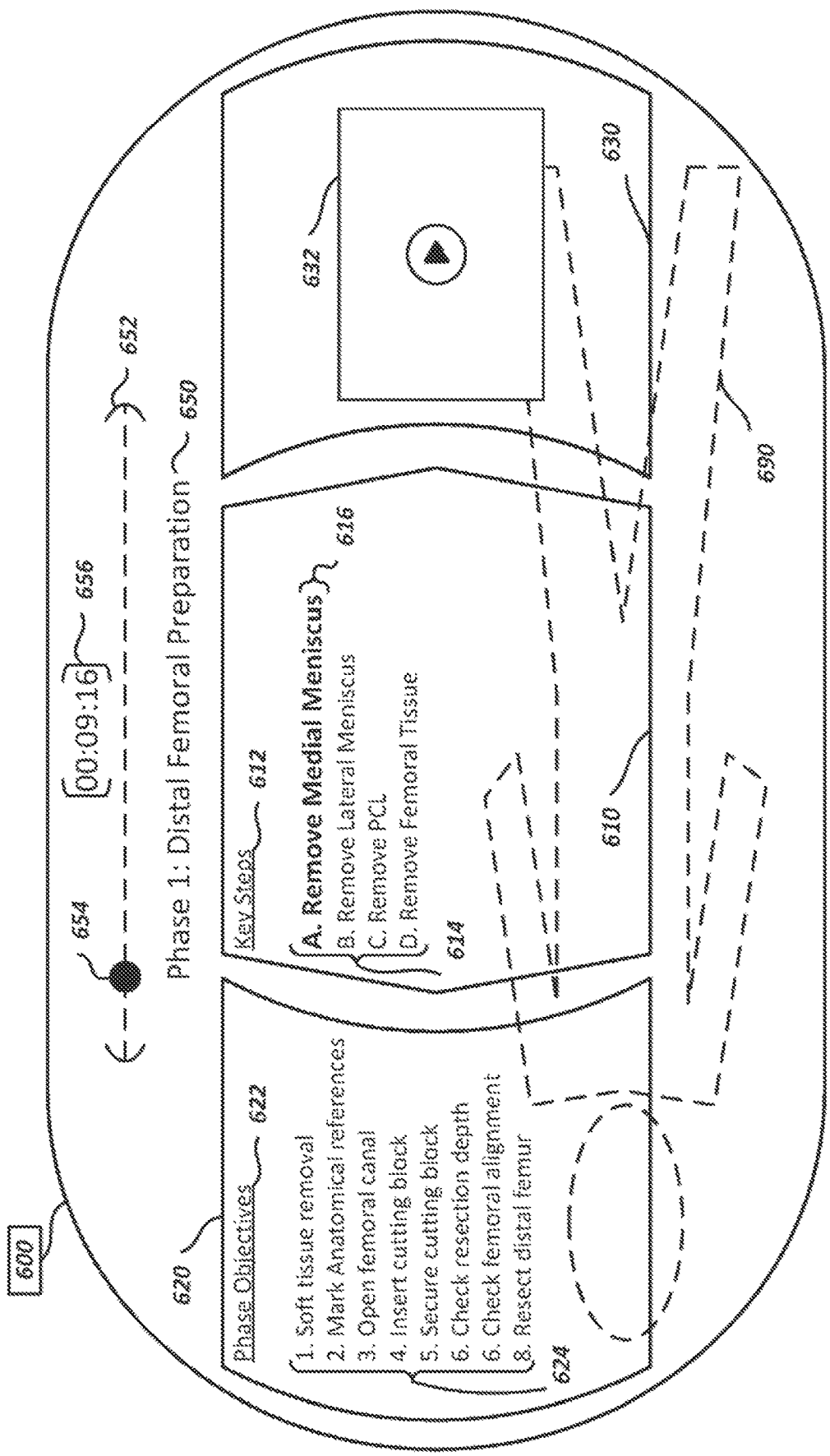
FIGS. 6A, 6B, and 6C show illustrations of the presentation of action guidance corresponding to the surgical data structure.
Figure 6B:
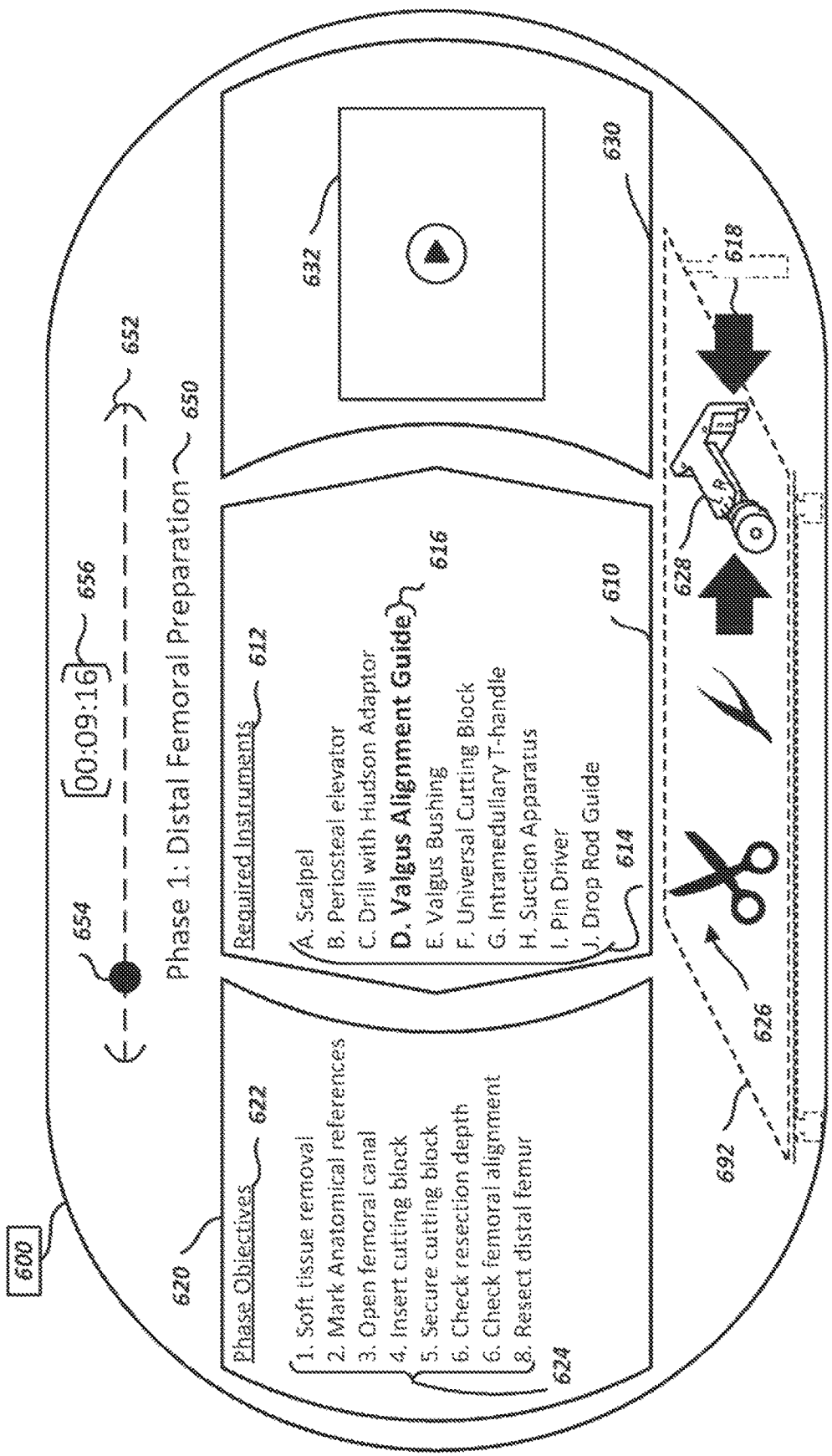
Figure 6C:
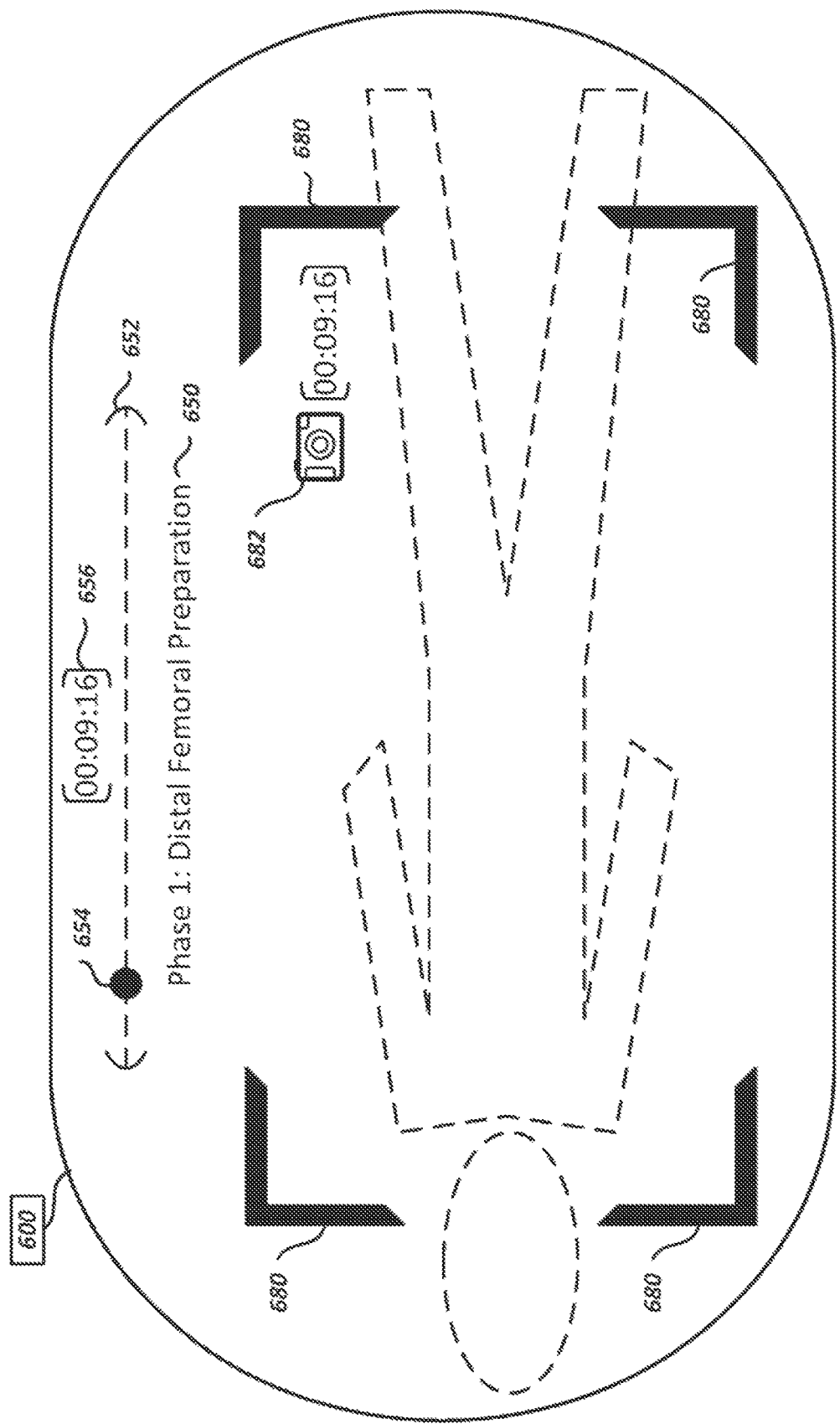

FIGS. 6A, 6B, and 6C illustrate embodiments of heads-up displays used to present surgical guidance to operating room personnel during a surgical procedure. The information presented may be included in metadata associated with a current node, a target node or an edge in the current surgical data structure. FIGS. 6A, 6B, and 6C illustrate views of the operating room from a surgeon or operating room personnel-mounted headset. In addition to presenting information, the headset may be equipped to collect live surgical data. For example, data may be collected via a camera, speaker, haptic sensor, and/or receiver (e.g., receiving data from a smart surgical tool). Data may be collected continuously or periodically (e.g., at defined times, at defined time intervals or upon detecting an event triggering collection).

In some embodiments, a processing device, such as the local server, may determine and continuously update a trajectory through the surgical data structure. The trajectory may be based on (for example) live surgical data, weights associated with nodes and edges the surgical data structure, changes in patient/surgery states, and/or a pre-programmed trajectory entered by a user. A user may enter a pre-programmed trajectory using a software application, such as a surgical map. The local server may transmit the trajectory data to (for example) one of the heads up displays and/or the control center to increase situational awareness.

FIG. 6A illustrates an augmented reality view 600 that can be used to present the steps associated with a surgical procedure from a surgeon's point-of-view (POV) heads-up display. The display can be semitransparent permitting the surgeon to see the patient 690 and surrounding operating room through the heads-up display. The graphics overlaid on the surgeon's POV include a primary display area 610, a first supporting display area 620, a second supporting display area 630, a title area 650, a procedural progress timeline 652 and indicator 654, and an elapsed time indicator 656. The display includes data retrieved from a surgical data structure. The local server can determine the relevant data based on live surgical data collected during a procedure.

The primary display area 610 may be used to present useful procedural information into the surgeon's field of view. Information in the primary display area may include (for example) identification of one or more actions, tools to be used, and/or expected results of an action. In some instances, data is presented in the primary display area 610, the first supporting display area 620, and/or the second supporting display area 630 only upon detecting a presentation-triggering event (e.g., that an orientation of a wearable device matches an orientation profile, that an acceleration of a wearable device matched an acceleration profile, or that a physical input of a predefined type was received).

In FIG. 6A, the primary display area includes a list of key steps associated with distal femoral preparation. The title 612 indicates that key steps are displayed. The steps are provided in a primary display list 614 with the current step highlighted 616. The first supporting display 620 includes a list of phase objectives. First supporting display title 622 indicates that content provided in first supporting display 620. The first supporting display list 624 is displayed to provide the surgeon with detailed phase objectives. The second supporting display 630 includes a video 632 of the current key step to be performed. The surgeon, operating room personnel, and/or the control center may remove any of the information from the field of view. The local server may automatically remove items from the surgeon's field of view based on surgical data received by the system.

FIG. 6B illustrates an augmented reality view 600 to present information associated with a surgical procedure to a non-surgeon operating room team member. The display can be semitransparent permitting the team member to see an operating room table 692, operating room instruments 626, and the surrounding operating room through the heads-up display. The graphics overlaid on the team member's POV include a primary display area 610, a first supporting display area 620, a second supporting display area 630, a title area 650, a procedural progress timeline 652 and indicator 654, and an elapsed time indicator 656.

The primary display area 610 may be used to present useful procedural information into the operating room team member's field of view. In FIG. 6B, the relevant operating room team member is a nurse. For a nurse, useful procedural information may include the required instruments for the current phase of a procedure. The title 612 on the nurse's primary display 610 reflects the difference in relevant information. the primary display list 614 lists the required instruments and the current instrument is highlighted 616. The augmented reality view 600 also includes an instrument indicator 618. The local server may use feature extraction from the associated headset's live video data to identify and highlight relevant instruments using an instrument indicator 618. The instrument 628 associated with the instrument indicator 618 may correspond to the highlighted 616 instrument on the primary display 610.

FIG. 6C illustrates an augmented reality view 600 used to capture a snapshot during the surgical procedure. A snapshot is useful for post-surgery analysis of the surgical procedure.

The snapshot view includes a title area 650, a procedural progress timeline 652 and indicator 654, an elapsed time indicator 656, a set of framing elements 680, and a visible timestamp 682.

In addition to the visual data captured by the snapshot in FIG. 6C, the local server may record additional data associated with the snapshot. Additional sensors that can provide additional data associated with the snapshot can include at least one operating room video camera, a microphone, an infrared sensor and an accelerometer. The additional sensors can be used to capture real-time data from the operating room including video, pictures, audio annotation, manual procedural step logging and user (e.g., surgeon, nurse or team member) notes. For example, the user may use the head mounted camera to capture image stills of critical steps of surgery for documentation of their practice in the event of an unexpected complication.

In some embodiments the captured images, and any other data associated with additional sensors captured during surgery can be stored against the active surgical procedure at the precise procedural location at which it was measured. This data may be used as, for example, an audit record, or training resource. Further, these sensors may facilitate user-system interactions, which may include gestures, voice commands, other form of hands-free interaction or direct hardware interactions such as buttons, or pedals, which may be separate to the headset but connected to structures and technologies described herein to provide real-time surgical guidance.

The guidance presented to the surgeon and operating room personnel is not limited to the embodiments shown herein. Surgical guidance may take the form of text commands, images (separate and/or overlaid on real-time video), augmented reality (AR) or virtual reality (VR) surgical guides (such as paths of incisions), informative animations (both AR, VR and separate from real image of surgery), haptic feedback and audio or visual commands or stimulus (e.g., signals, alarms, music, and ambient light change).

Figure 7:
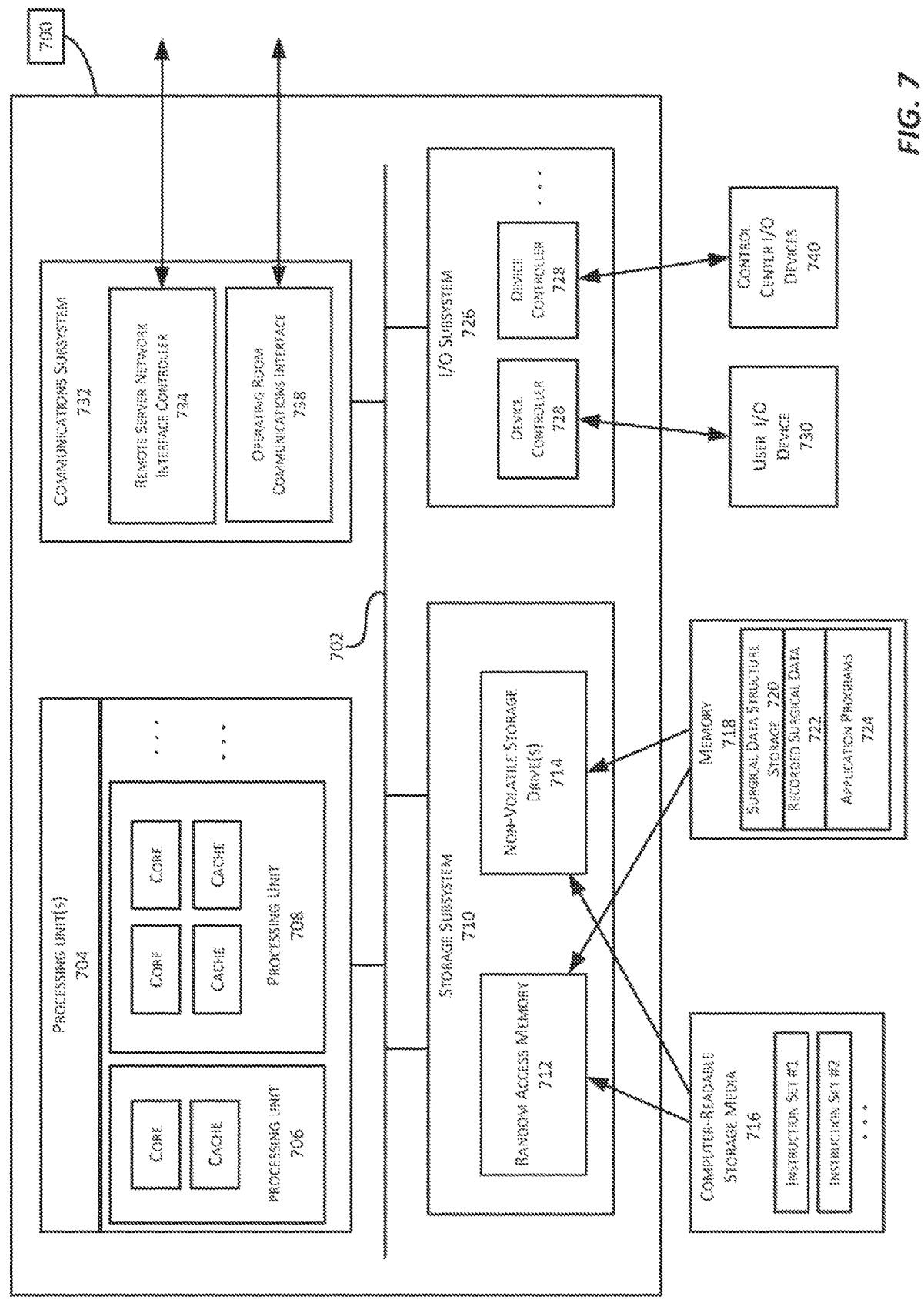
FIG. 7 shows a block diagram of an embodiment of a local server configured to provide surgical guidance using a surgical data structure.

With reference to now to FIG. 7, a block diagram of an illustrative surgical navigation local server 700 is shown. The local server 700 may correspond to the local server 170 described above. Local server 700 includes processing units 704 that communicate with a number of peripheral subsystems via a bus subsystem 702. These peripheral subsystems include, for example, a storage subsystem 710, an I/O subsystem 726, and a communications subsystem 732.

Bus subsystem 702 provides a mechanism for letting the various components and subsystems of local server 700 communicate with each other. Although bus subsystem 702 is shown schematically as a single bus, alternative embodiments of the bus subsystem may utilize multiple buses. Bus subsystem 702 may be of any several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which may be implemented as a Mezzanine bus manufactured to the IEEE P1386.1 standard.

Processing unit 704, which may be implemented as one or more integrated circuits (e.g., a microprocessor or microcontroller), controls the operation of local server 700. Processing unit 704 may be implemented as a special purpose processor, such an application-specific integrated circuit (ASIC), which may be customized for a particular use and not usable for general-purpose use. In some implementations, an ASIC may be used to increase the speed of feature extraction from live surgical data. In some embodiments, processing unit 704 may include one or more graphics processing units (GPUs). The GPUs may be configured to process live surgical data in order to perform feature extraction. One or more processors, including single core and/or multicore processors, may be included in processing unit 704. As shown in FIG. 7, processing unit 704 may be implemented as one or more independent processing units 706 and/or 708 with single or multicore processors and processor caches included in each processing unit. In other embodiments, processing unit 704 may also be implemented as a quad-core processing unit or larger multi core designs (e.g., hexacore processors, octo-core processors, ten-core processors, or greater). In some embodiments, one or more independent processing units may be replaced with an ASIC optimized for feature extraction.

Processing unit 704 may execute a variety of software processes embodied in program code, and may maintain multiple concurrently executing programs or processes. At any given time, some or all of the program code to be executed may be resident in processor(s) 704 and/or in storage subsystem 710. In some embodiments, local server 700 may include one or more specialized processors, such as digital signal processors (DSPs), outboard processors, graphics processors, application-specific processors, and/or similar specialized processors.

I/O subsystem 726 may include device controllers 728 for one or more user interface input devices and/or user interface output devices. I/O devices can include a user (e.g., surgeon, nurse or team member) I/O device 730 for use by a user pre, during or post-surgery. A surgical data structure explorer can be executed on the user I/O device 730. The user I/O device 730 can provide a user the capability to adjust the preferred route, procedural metadata, assigned weights, and/or other data associated with a surgical data structure prior to surgery. Post-surgery a user may use the user I/O device 730 to review the analysis performed by a processing device. In some embodiments, the I/O devices can include control center I/O devices 740.

User interface input and output devices may be integral with local server 700 (e.g., integrated audio/video systems, and/or touchscreen displays), or may be separate peripheral devices which are attachable/detachable from local server 700. The I/O subsystem 726 may provide one or several outputs to a user by converting one or several electrical signals to user perceptible and/or interpretable form, and may receive one or several inputs from the user by generating one or several electrical signals based on one or several user-caused interactions with the I/O subsystem such as the depressing of a key or button, the moving of a mouse, the interaction with a touchscreen or trackpad, the interaction of a sound wave with a microphone, or similar user inputs.

Input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices 730 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, haptic devices, and eye gaze tracking devices. Additional input devices may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, electromagnetic sensors configured to detect movement of surgical tools, optical sensors, near infrared sensors, and similar devices.

Output devices may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, haptic devices, and the like. In general, use of the term "output device" is intended to include all possible types of devices and mechanisms for outputting information from local server 700 to a user or other computer. For example, output devices may include, without limitation, a variety of display devices that visually convey text, graphics and audio/video information such as monitors, printers, speakers, headphones, automotive navigation systems, plotters, voice output devices, and modems.

Local server 700 may comprise one or more storage subsystems 710, comprising hardware and software components used for storing data and program instructions, such as system memory 718 and computer-readable storage media 716. The system memory 718 and/or computer readable storage media 716 may store program instructions that are loadable and executable on processing units 704, as well as data generated during the execution of these programs. Program instructions may include instructions to perform one or more actions or part(s) or all of one or more methods or processes described herein. For example, program instructions may include instructions for identifying a discrete surgical procedural state. Program instructions may include instructions for generating, transmitting, and/or receiving communications. Program instructions may include instructions for automated processing. Program instructions may include instructions for generating automated processing and/or stage results. Program instructions may include instructions for performing a work flow iteration.

Depending on the configuration and type of local server 700, system memory 718 may be stored in volatile memory (such as random access memory (RAM) 712) and/or in non-volatile storage drives 714 (such as read-only memory (ROM), flash memory, etc.) The RAM 712 may include data and/or program modules that are immediately accessible to and/or presently being operated and executed by processing units 704. In some implementations, system memory 718 may include multiple different types of memory, such as static random access memory (SRAM) or dynamic random access memory (DRAM). In some implementations, a basic input/output system (BIOS), including the basic routines that help to transfer information between elements within local server 700, such as during start-up, may typically be stored in the non-volatile storage drives 714. By way of example, and not limitation, system memory 718 may include surgical data structure storage 720, recorded surgical data 722, and application programs 724 such as feature extraction applications, procedural state identification applications, headset display applications, surgical data structure explorer applications, user applications, mid-tier applications, server applications, etc.

Storage subsystem 710 also may provide one or more tangible computer-readable storage media 716 for storing the basic programming and data constructs that provide the functionality of some embodiments. Software (programs, code modules, instructions) that when executed by a processor provide the functionality described herein may be stored in storage subsystem 710. These software modules or instructions may be executed by processing units 704. Storage subsystem 710 may also provide a repository for storing data used in accordance with the embodiments illustrated herein.

Storage subsystem 710 may also include a computer-readable storage media reader that may further be connected to computer-readable storage media 716. Together and, optionally, in combination with system memory 718, computer-readable storage media 716 may comprehensively represent remote, local, fixed, and/or removable storage devices plus storage media for temporarily and/or more permanently containing, storing, transmitting, and retrieving computer-readable information.

Computer-readable storage media 716 containing surgical data structures, program code, or portions of program code, may include any appropriate media known or used in the art, including storage media and communication media, such as but not limited to, volatile and non-volatile, removable and nonremovable media implemented in any method or technology for storage and/or transmission of information. This may include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This may also include nontangible computer-readable media, such as data signals, data transmissions, or any other medium that may be used to transmit the desired information and that may be accessed by local server 700.

By way of example, computer-readable storage media 716 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray disk, or other optical media. Computer-readable storage media 716 may include, but is not limited to, Zip drives, flash memory cards, universal serial bus (USB) flash drives, secure digital (SD) cards, DVD disks, digital video tape, and the like. Computer-readable storage media 716 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for local server 700.

Communications subsystem 732 may provide a communication interface from local server 700 and remote computing devices via one or more communication networks, including local area networks (LANs), wide area networks (WANs) (e.g., the Internet), and various wireless telecommunications networks. As illustrated in FIG. 7, the communications subsystem 732 may include, a remote server network interface controller (NIC) 734. The NIC may be an Ethernet card, Asynchronous Transfer Mode NICs, Token Ring NICs or a similar interface. The communications subsystem 732 may include one or more wireless interfaces, including an operating room communications interface 738. The operating room communications interface 738 may be implemented using a wireless network interface controller. Additionally and/or alternatively, the communications subsystem 732 may include one or more modems (telephone, satellite, cable, ISDN), synchronous or asynchronous digital subscriber line (DSL) units, FireWire interfaces, USB interfaces, and the like. Communications subsystem 732 also may include radio frequency (RF) transceiver components for accessing wireless voice and/or data networks (e.g., using cellular telephone technology, advanced data network technology, such as 3G, 4G or EDGE (enhanced data rates for global evolution), Wi-Fi (IEEE 802.11 family standards, or other mobile communication technologies, or any combination thereof), global positioning system (GPS) receiver components, and/or other components. A cellular enabled local server 700 may be used in austere conditions where users (e.g., surgeon, nurse or team member) may traditionally have limited access to traditional methods of surgical guidance.

The various physical components of the communications subsystem 732 may be detachable components coupled to the local server 700 via a computer network, a FireWire bus, a serial bus, or the like, and/or may be physically integrated onto a motherboard or circuit board of local server 700. Communications subsystem 732 also may be implemented in whole or in part by software.

In some embodiments, communications subsystem 732 may also receive input communication in the form of structured and/or unstructured data feeds, event streams, event updates, and the like, on behalf of one or more devices that may use or access local server 700. For example, communications subsystem 732 may be configured to receive data feeds associated with surgical data or surgical data structures in real-time from other communication services, web feeds such as Rich Site Summary (RSS) feeds, and/or real-time updates from one or more third party information sources. Additionally, communications subsystem 732 may be configured to receive data in the form of continuous data streams, which may include event streams of real-time events and/or event updates (e.g., surgical data, surgical data structure updates, preferred route updates, patient updates, etc.). Communications subsystem 732 may output such structured and/or unstructured data feeds, event streams, event updates, and the like to one or more data stores that may be in communication with device 700.

Due to the ever-changing nature of computers and networks, the description of local server 700 depicted in FIG. 7 is intended only as a specific example. Many other configurations having more or fewer components than the device depicted in the figure are possible. For example, customized hardware may also be used and/or particular elements may be implemented in hardware, firmware, software, or a combination. Further, connection to other computing devices, such as network input/output devices, may be employed. Based on the disclosure and teachings provided herein, it will be appreciated that there are other ways and/or methods to implement the various embodiments.

Figure 8:
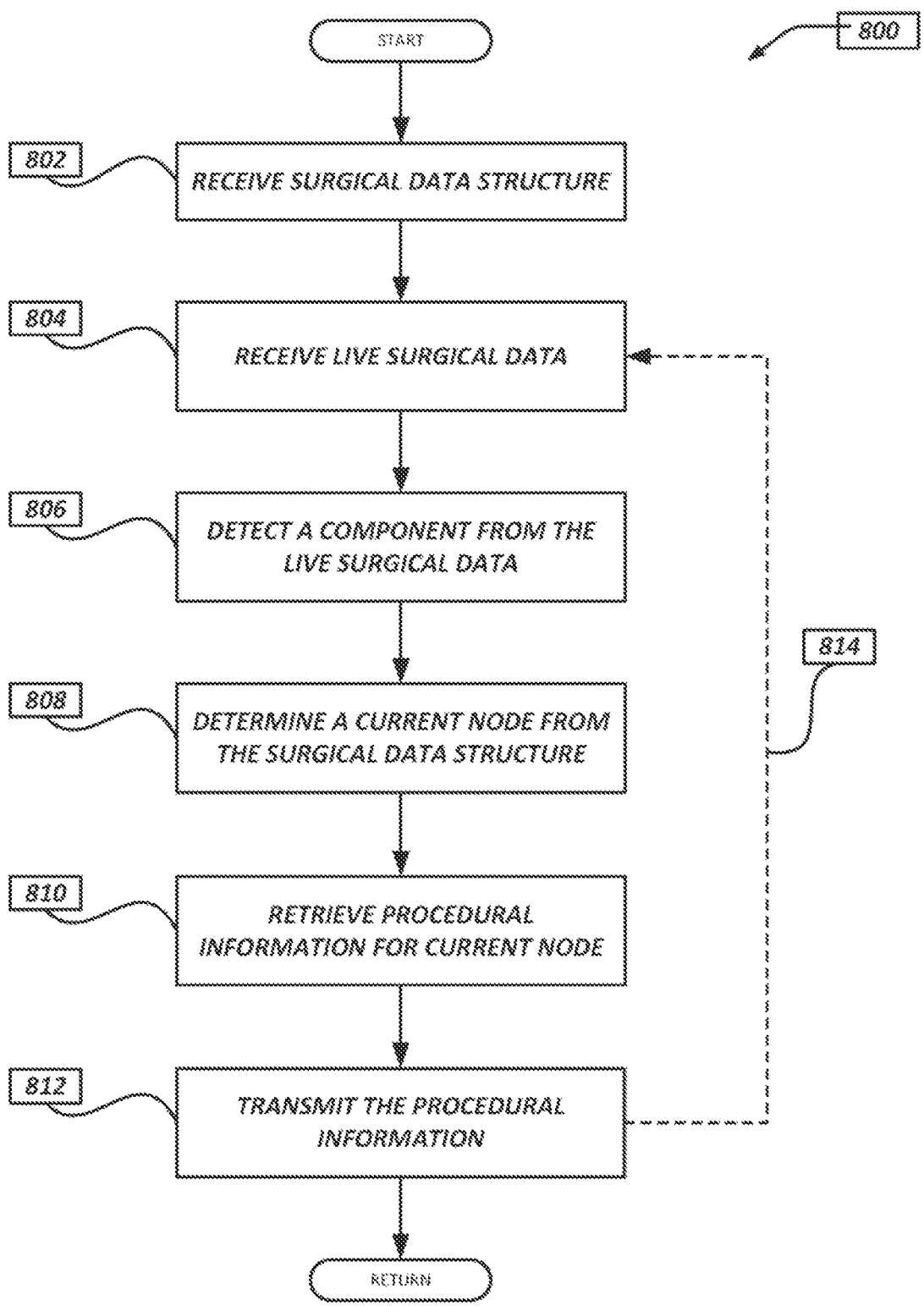
FIG. 8 shows a flowchart of a method for the automated provisioning of real-time custom procedural surgical guidance.

Referring next to FIG. 8, a flowchart of a process 800 for the automated provisioning of real-time custom procedural surgical guidance 800 is illustrated. The method for the automated provisioning of real time custom procedural guidance includes a plurality of steps connected with directional arrows. The directional arrows not only indicate that the elements are connected, but also indicate the direction that data may flow with respect to the various elements. For example, first, the method receives a surgical data structure 802. For example, the surgical data structure may be received from another remote device (e.g., cloud server), stored and then retrieved prior to or during performance of a surgical procedure. The surgical data structure can provide precise and accurate coded descriptions of complete surgical procedures. The surgical data structure 802 can describe routes through surgical procedures and is described in detail above with reference to FIG. 2. For example, the surgical data structure 802 can include multiple nodes, each node representing a procedural state (e.g., corresponding to a state of a patient). The surgical data structure 802 can further include multiple edges, with each edge connecting multiple nodes and representing a surgical action.

After receiving the surgical data structure, live surgical data is received at block 804. In certain embodiments, live surgical data 804 may include user inputs, a video stream, or operating room data. As one illustration, user inputs may include manual inputs directly provided by operating room personnel (e.g., via a wearable device or non-wearable device located inside or near an operating room). For example, operating room personnel may include the performing surgeon, a nurse, an anesthetist, or remote surgeon watching the procedure. Inputs may include gesture, voice, another form of hands-free sterile interaction and even direct contact with a computer user-interface. As another (additional or alternative) illustration, live surgical images may be recorded, such as those captured on video from a head-mounted surgeon camera. As yet another (additional or alternative) illustration, live surgical data 804 may include other operating room data such as; time elapsed in procedure, nodes already passed by the users (e.g., surgeon, nurse or team member), identified surgical instruments used or in use, personnel present in the operating room and user movements measured from accelerometers in a guidance system headset or other system-connected wearable devices.

At block 806, a component is detected from the live surgical data. In some embodiments, the method detects a component from the live surgical data 806 using feature extraction. Anatomic feature extraction can be performed on the live surgical images to detect an anatomic state, anatomic pose, or any other attribute possible to derive from video that can be used later to determine a precise procedural state. Additional data such as user input or operating room data may assist with feature extraction. The feature extraction algorithm used to detect a component from the live surgical data may include machine learning iterations. In particular, if the first implementation of the systems and methods described herein requires manual navigation through the procedure by the user (e.g., surgeon, nurse or team member), the resulting dataset of live surgical images and associated navigation commands can be used as an effective algorithm training resource using machine learning software. In other embodiments, a component may be associated with a user input or operating room data.

At block 808, a current node from the surgical data structure is identified. In some embodiments, the current node will correspond to the component detected from the live surgical data. For example, a component may identify a patient state, which may indicate which of multiple nodes corresponds to a current circumstance. In other embodiments, an edge may correspond to the component detected in the live surgical data. The current node and the component may correspond to a discrete procedural state. In other embodiments, the user input or the operating room data may be used to determine the current node from the surgical data structure.

At block 810, procedural information for the current node is retrieved. For example, each of one, more or all nodes may have particular procedural information associated with the node, and some or all of the particular procedural information may be retrieved. As another example, a current node may be connected to each of one or more next-stage nodes via a corresponding edge. An edge may have particular procedural information associated with the edge, and some or all of the particular procedural information may be retrieved. Procedural information can include a description of and/or information corresponding to a patient state that fully describes the condition of a patient at a given point during a medical procedure. Procedural information may include (for example) pose, anatomical state, initial preparation and/or sterilization information. In some embodiments, the quantity of procedural information to be provided may be tailored e.g., to lower operating room personnel information workload.

At block 812, the procedural information is transmitted. In some embodiments, the method may transmit the procedural information to a wearable device used by one or more operating room personnel. In some embodiments, the process 800 can return from block 814 to receiving live surgical data at block 804 and then repeat the blocks to detect components 806, determine a new current node 808, retrieve procedural information for the current node 810, and again transmit the procedural information 812 for the current node. In some embodiments, the structures and technologies described herein may transmit the procedural information 812 based on a contingent event such as low point in operating room activity or an input form the surgeon or the operating room personnel.

Figure 9:
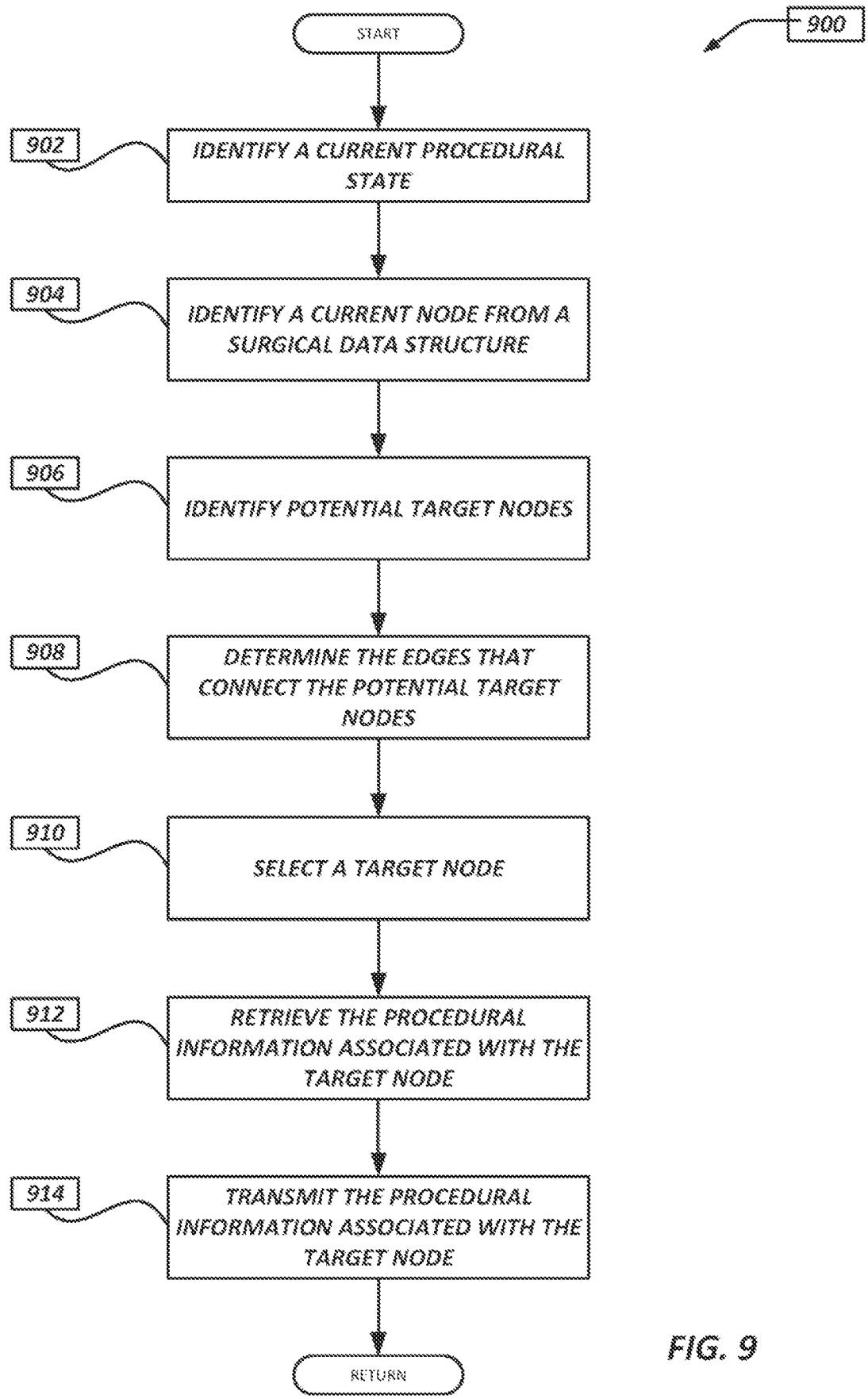
FIG. 9 shows a flowchart of a method for selecting a target node.

The structures and technologies described herein may provide real time recommendations of surgical actions based on live data as described in process 900, as depicted in FIG. 9. At block 902, a procedural state is identified. For example, a node may be identified from amongst multiple nodes represented in a surgical data structure. The identified node may correspond to a discrete procedural state corresponding to a current circumstance (and/or recently received live data) of a surgical procedure.

At block 906, one or more potential target nodes are identified. Each potential node can be connected (e.g., directly connected) to the current node by an edge, which can be identified at block 908. Each of the one or more potential target nodes may include a node connected (e.g., directly connected) to the current node. Each of the one or more potential target nodes and/or each node connecting the current node to a potential node of the one or more potential target nodes may be associated with one or more variables, such as a weight, representing, for example, a potential surgical outcome, surgical risk, outcome probability and/or predicted time commitment. Surgical risk may represent the predicted probability of an unfavorable outcome occurring at any point during surgery. Surgical risk may represent the probability of complications in a node-to-node transition.

The variable(s) may have been generated based on (for example) an outcome of one or more real surgical procedures recorded by the guidance system, knowledge of outcome from annotated libraries of surgical videos and/or even appropriately tagged academic research relating to specific surgeries or surgical steps. For example, a plurality of intra-surgical indicators may be used to assess surgical risk and/or potential surgical outcomes. Direct surgical indicators may include, among other things, patient blood loss. The structures and technologies described herein may determine a patient who has undergone significant loss of blood is at more risk than one who has reached the same point in the procedure with less blood lost. Indirect surgical risk indicators may include, among other things, which instrument is being used, whether surgery is currently active near delicate anatomical structures and even simply the time spent by the surgeon on each individual surgical step.

Further, surgical risk may also be stratified by patient specific data. Patient information such as age, weight, prior surgical interventions and health history may further inform the calculation of surgical risk. Using collected metadata and other sources of risk indicators, such as academic research, associations and relevant 'weightings' of each of at least one of the one or more variables may be determined between patient specific data (e.g., age) and live surgical parameters at specific procedural-steps (e.g., blood loss during a specific phase of liver surgery).

The weighting of patient specific parameters may then be used to interpret live surgical data to perform a selection of a target node at block 910. The target node need not be a final node of the data structure may correspond to a next (e.g., directly connected node). For example, a selection may be made to maximize (an outcome variable) or minimize a surgical risk or to maximize a score calculated based on a combination of multiple of the one or more variables.

At block 914, procedural information associated with the target node 912 can be retrieved and transmitted (e.g., to a device present in or near an operating room or location associated with the surgical procedure).

Figure 10:
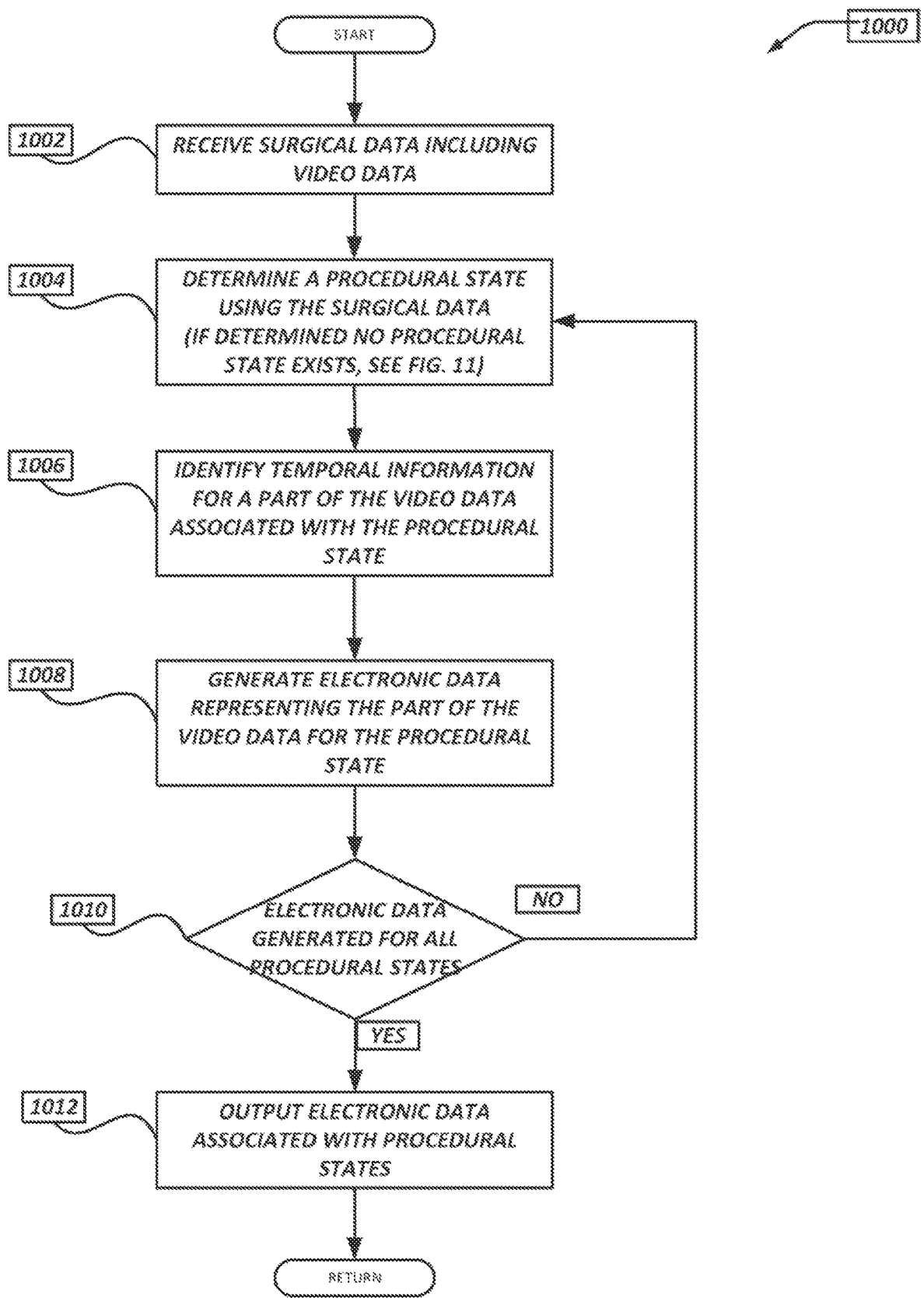
FIG. 10 shows a flowchart of a method for analyzing surgical data and outputting electronic data associated with procedural states.

FIG. 10 shows a process 1000 for using live surgical data for tracking and procedural models. At block 1002, surgical data is received. The surgical data can include data collected during a performance of a surgery. The surgical data can include digital video data, which may include a continuous signal that represents moving visual images. The video data may, but need not, include an audio signal that is aligned with the visual signal. The surgical data may (e.g., alternatively or additionally) include audio data, representations of one or more inputs received at a device (e.g., a voice command, a motion command or input received at a keyboard or other interface component), data from a smart surgical tool (e.g., indicative of a location, movement and/or usage), and so on. The surgical data can include data collected from a single device or from multiple devices. The surgical data can include data collected over a time period (e.g., a predefined time increment, since a previous state-transition time or procedure initiation time, or a time of an entire surgical procedure). The surgical data may include raw data collected during the surgery or a processed version thereof (e.g., to reduce noise and/or transform a signal, such as transforming accelerometer data collected at a headset to a movement command indicating that the surgical procedure has progressed to a next step).

At block 1004, a procedural state is determined using all or part of the surgical data. In some instances, the surgical data is incrementally received (e.g., as it is collected in real-time), and surgical data can then be incrementally processed (e.g., by separately processing each data increment or by aggregating a recently received data increment with other data, such as data from a previous time increment or from another device, and processing the aggregated data). In these instances, a state may be determined for the new data (or aggregated data).

In some instances, the surgical data may include a larger data set that may represent multiple states. For example, a larger data set may include a continuous data set (e.g., video collected over the course of a surgical procedure). The surgical data may then be divided into multiple chunks (e.g., of a predefined duration), and a state may be determined for each chunk. Thus, for example, block 1004 may be performed multiple times.

The chunks may, or may not, be overlapping. When chunks are overlapping, an offset time by which the chunks advance may also be predefined. For example, in a 2-hour procedure, a video stream may be segmented into 60 two-minute, non-overlapping segments. As another example, in a 2-hour procedure, a video stream may be segmented to procedure 119 two-minute segments, where each segment overlaps with a previous segment by 1 minute. In some instances, surgical data includes a discrete data set. Discrete data points may be individually analyzed or binned into one of multiple time windows (e.g., which may, or may not be overlapping and may have a predefined duration), such that each discrete data point may be assessed in combination with other discrete data points and/or a chunk of each of one or more continuous data sets that correspond to a same time window. In some instances, surgical data includes deterministic indicators of state transitions, such as a command received from a user indicating transition to a new state. Time windows may then be defined as times between these transitions, and other surgical data may be binned in accordance with times associated with the data.

Determining the procedural state may include, for example, selecting a single node (or one or more nodes) from amongst a plurality of nodes in a surgical data structure. The surgical data structure can include one associated with a particular type of surgery being conducted (e.g., and may be identified based on input received before, during or after the surgery and/or based on a patient record or operating room schedule that identifies a type of surgical procedure being performed). The state may be identified as one that correspond with the selected node(s). In some instances, each node of a structure's plurality of nodes include one or more live-data signatures that include one or more characteristics of live data that are associated with the node. A characteristic may include (for example) a value identifier (e.g., identifying a particular word command), a definition of a range (e.g., for a distance expected between two particular devices), a threshold (e.g., a lower threshold for an acceleration value from a surgical tool), and so on. The determination at block 1004 may include determining to which node's signature the received data most closely corresponds (and/or corresponds with to at least a threshold degree). In some instances, the determination can be constrained, such that only a subset of the plurality of nodes are considered (e.g., those nodes of the plurality of nodes that are directly connected to a node associated with a current state). For example, the constraint may be such to not allow a determination that a "Surgery-Complete" state would immediately follow a "Surgery-Begins" state.

Various transformation, detection and/or extraction techniques may be used to identify to which node the surgical data corresponds. For example, a model generated based on performance of a machine-learning algorithm may be used to process the video data to identify the one or more procedural states. As another example, audio cues from the video may be assessed to identify the state(s). As yet another example, detecting that a particular tool is being used (e.g., based on a movement signal or activation signal received from the tool or based on detecting that the tool is being moved to a location overlapping with a patient location based on video data) may be used to identify the state(s).

It will be appreciated that one or both of blocks 1002 and 1004 may be performed during a surgical procedure (e.g., at a local surgery in an operating room or facility at which the procedure is being performed or at a remote server, such as a cloud server) or after the procedure using stored data collected during the procedure. For example, in one instances, surgical data is collected during a surgical procedure by devices located in an operating room, and subsequently a remote server may receive and process the surgical data. As another example, a local device may receive and process the surgery data during the procedure.

In some embodiments, block 1004 may determine that the surgical data structure does not include a procedural state that is associated with the surgical data received at block 1002. Block 1004 may identify that the surgical data is associated with a new procedural state. In some embodiments, block 1004 may generate a new node using the process described in FIG. 11. An update to the nodes and procedural states identified in the surgical data structure may be initiated automatically by a local or remote server or by a user input. The user input may be entered by, for example, a user in the control center with access to a local server configured to execute surgical data structure explorer.

At block 1006, temporal information is identified for a part of the video data associated with the procedural state. The temporal information may include (for example) a start time, end time, duration and/or range. The temporal information may be absolute (e.g., specifying one or more absolute times) or relative (e.g., specifying a time from a beginning of a surgery, from a beginning of a procedure initiation, etc.). The temporal information may include information defining a time period or time corresponding to the video data during which it is estimated that the surgery was in the procedural state.

The temporal information may be determined (for example) based on information associated with the state identification. For example, if surgery data is divided into data chunks, and each data chunk is associated with a procedural state, the temporal information may identify a start and end time that corresponds to (for example) a start time of a first data chunk associated with a given procedural state and an end time of a last data chunk associated with a given procedural state, respectively. As another example, if discrete data points are received that are indicative of state transitions, the temporal information may include times associated with two consecutive data points. As yet another example, a data set may be analyzed to detect state transitions (e.g., by detecting activation/inactivation of a particular smart tool, detecting a time period during which a particular visual characteristic is detected in video data, detecting times at which an audio command is detected in an audio signal that indicates that a state is transitioning, etc.). It will be appreciated that transitions between different states may have a same or different transition characteristic.

At block 1008, electronic data is generated representing the part of the video data for the procedural state. The electronic data may include information included in or identified by (e.g., via a location identification) metadata of a node associated with the procedural state in a surgical data structure. The electronic data may (for example) identify the procedural state (e.g., by identifying a state of a patient, progress of a surgery, etc.), identify an action that is being performed or is about to be performed (e.g., as identified in an edge that connects a node corresponding to the procedural state with a node corresponding to a next procedural state), and/or identify one or more considerations (e.g., a risk, tools being used or that are about to be used, a warning, etc.). The electronic data may relate to a trajectory. For example, electronic data may indicate when an action is being performed that is contrary to (or, in other instances, in accordance with) a typical action, recommended action, or action prescribed by a guideline at a state of surgery.

The electronic data may include (for example) data that is to be concurrently presented during presentation of at least part of the part of the video data. For example, the electronic data may include text (e.g., an annotation) that is to be overlaid or presented next to a visual display of the part of the video data. As another example, the electronic data may include an audio signal (e.g., of spoken words) that is to be presented during a visual display of the part of the video data. Any audio data in the video signal may be, for example, eliminated, softened or maintained.

At block 1010, it is determined whether electronic data has been generated for all procedural states. If electronic data does not exist for all the procedural states, process 1000 returns to block 1004 or 1006, where a next procedural state is determined or where temporal information is identified for another part of the video data associated with a next procedural state.

If electronic data exists for all procedural states, process 1000 continues to block 1012, where the electronic data (e.g., generated for each procedural state) is output. In some instances, the electronic data is aggregated across states. For example, modified video data may be generated that includes the electronic data generated for each procedural state. The modified video data may include all or part of original video data but with additional presentations of electronic data that represents a procedural state represented in a displayed part of the video signal. For example, if a one-hour surgery included six procedural states—each associated with successive, non-overlapping 10-minute time windows, modified surgery data may include a 60-minute visual signal accompanied by an annotation that changes every 10 minutes or that appears (with new text every ten minutes). As another example, for the same hypothetical surgery, an annotation may repeatedly change (e.g., every minute) during the video, but the text may always be text associated with a procedural state associated with a current image being displayed. As yet another example, a video signal may be parsed to identify a predefined number of images (e.g., 1 or a number greater than 1) associated with each procedural state, and a document may be generated that includes the images and text near the images that identify an action being performed.

The output may include transmitting the electronic data (e.g., in association with an identifier of the video data or surgical procedure) to storage or another device. In some instances, the temporal information is used to annotate and/or assess video data. For example, it may be determined whether a surgical team traversed through an approved set of actions. As another example, a video may be annotated with captions to identify what steps are being performed (e.g., to train another entity).

The electronic data generated using process 1000 may provide a base to describe surgical consensuses and assess individual procedural compliance. Contingent on the ability to define a discrete route through a surgical data structure for a given procedure is the possibility to compare two separate routes. As individual surgical data structures are coded, not textual descriptions, process 1000 provides data useful to directly quantify the differences between two sets of live surgical data. The comparison represents the difference in the defining attributes of nodes and actions coded within the two procedures. Further to these attributes, the comparison may also include metadata recorded against the map such as risk induced during the procedure.

In some embodiments, these data points may include, for example information relating the surgical data structure such as anatomical modifications made not within the original surgical route, time taken for each step and the types of instrument used, or data retrieved from patient measurements made during the procedure such as blood loss or loss of heart beat during the procedure.

In certain embodiments, a surgical route is identified based on live surgical data. The surgical route can then be compared to a pre-computed procedural profile (e.g., identifying one or more recommended or required procedure characteristics. A metric of procedural compliance may be generated. This metric of procedural guidance represents a quantitative analysis of how well a canonical procedure method was followed. In some embodiments, the metric may be used for training or education purposes. The metric may be generated using an "ideal" surgical data structure, which can be used to provide a procedural compliance score.

In some embodiments generating electronic data associated with procedural states enables auto-editing of surgical video and other material to streamline the design of accurate training tools. Using procedural step recognition 1004, videos may be annotated, tagged or edited to become more easily navigable as a training tool. Furthermore, this functionality may be used to efficiently reduce the volume of data needed to be stored to contain all the crucial steps of surgery. Currently the process of surgical video editing is highly labor intensive and requires manual annotation or editing to produce an educational surgical video.

In additional embodiments, a defined surgical data structure route may be used to produce other training tools. By definition, a surgical data structure holds all the information needed to reproduce a surgical procedure, including a detailed anatomical reference model. Therefore, the data held in the specific sequence of particular actions and nodes referenced within this route may be reproduced or simulated in video, an AR format, or a VR format to produce comprehensive surgical simulations or animations. Further, these training simulation tools may be adjusted to provide a pre-operative training tool. By integrating patient specific data to a generic 4D surgical map or surgical data structure of a procedure, the resulting simulation may be used to refresh a surgeon or other entity involved in a surgical procedure of the preferred surgical method prior to a procedure.

Figure 11:
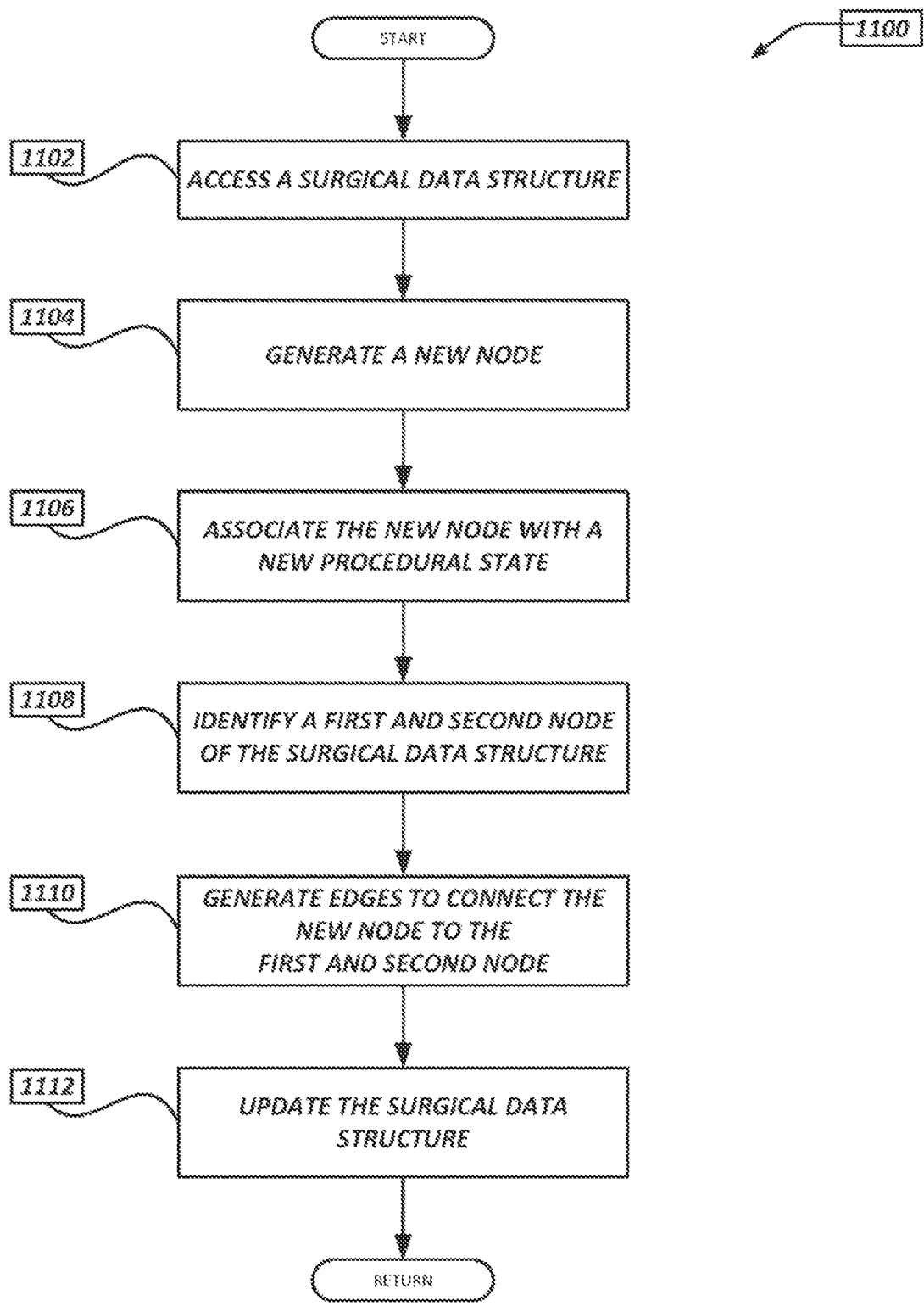
FIG. 11 shows a flowchart of a method for updating a surgical data structure.

FIG. 11 shows a process 1100 for updating the surgical data structure. At block 1102, a surgical data structure is accessed. In some embodiments, the surgical data structure is similar to the examples discussed in relation to FIGS. 2, 3, and 4.

At block 1104, a new node is generated for the surgical data structure. A new node may be generated in response to detecting that a node-creation condition was satisfied. The node-creation condition may be configured to be satisfied upon detecting input that corresponds to an instruction to add a node to the surgical data structure (e.g., with an identification of a corresponding state and/or surgical action). An update to the node-creation condition can be initiated pre-surgery, during surgery, or post-surgery by (for example) an automated process and/or a manual input from a user accessing the surgical data structure.

In some embodiments, an update to the node-creation condition can be initiated by an automated process. A local server, a remote server, or another computing device can include instructions that configure the device to execute an automated process to update the node-creation condition. The automated process to update the node-creation condition can access surgical data from a single procedure or a dataset that includes surgical data from multiple procedures. The surgical data can include any of the types of data discussed in relation to block 1002 of FIG. 10. The automated process to update the node-creation condition can process the surgical data into one or more discrete data points. The discrete data points can be associated with video data, audio data, representations of inputs received at a device (e.g., a voice command, a motion command or input received at a keyboard or other interface component), data from smart surgical tools, and so on. The discrete data points may be identified from the surgical data using a feature extraction algorithm. In some embodiments, the automated process to update the node-creation condition may receive the discrete data points from another process associated with providing surgical guidance.

After processing the surgical data into one or more discrete data points, the automated process to update the node-creation condition may determine that one or more of the discrete data points do not correspond to a procedural state associated with a node in the surgical data structure. If the discrete data points do not correspond to a node in the surgical data structure, the automated process to update the node-creation condition may configure the node-creation condition to be satisfied. In some embodiments, the process may be configured to transmit a request for approval to trigger the node-creation condition to an appropriate approval authority prior to updating the node-creation condition.

In some embodiments, the node-creation condition may be satisfied manually. A user (e.g., surgeon, nurse or team member) may access surgical data using a surgical data structure explorer. The surgical data structure explorer can be configured to provide a user access to surgical data associated with a surgical data structure. The user may provide inputs to the surgical data structure explorer that satisfy the node-creation condition. The user inputs can include, for example, a new procedural state, discrete data points associated with the surgical data, and/or additional information that the process can use to generate a new node.

After the node creation condition is satisfied by the automated process or manually, a new node can be generated for the surgical data structure. The new node will be associated with new procedural metadata. The procedural metadata can include any of the data discussed earlier in the specification. The process can identify procedural metadata to be associated with the new node from the one or more discrete data points extracted from the surgical data. The process can also receive procedural metadata from a user's manual inputs.

At block 1106, the new node can be associated with a new procedural state. The generation of the new node and/or association with the new procedural state may be based on (for example) one or more of user inputs, sensor data from a device (e.g., wearable or non-wearable device) located in an operating room, data from a smart surgical tool, and/or data from a camera recording video data in an operating room. For example, a set of instructions, executable on the local server, remote server, and/or a computing device, can include instructions to update the surgical data structure to include a new procedural state associated with the one or more discrete data points extracted from the surgical data. Further instructions may update the surgical data structure to associate the new node generated in at block 1104 with the new procedural state. A computing device accessing the updated surgical data structure can identify the new node by determining received surgical data includes discrete data points that match discrete data points associated with the new procedural state.

The new node generated at block 1104 can be integrated into the surgical data structure. At block 1108, a first node and second node of the surgical data structure 1108 that are related to the new node are identified. The first node can include one representing a procedural state preceding the new procedural state (e.g., corresponding to a time before a particular action was performed). The second node can include one representing a procedural state occurring after the new procedural state (e.g., corresponding to a time after a different particular action is performed). It will be appreciated that, in some instances, more than one first node and/or more than one second node is identified.

In some embodiments, the related nodes can be determined using the associated procedural metadata. In some instances, only a subset of the variables in the procedural metadata associated with a node may include values different from a second node in the surgical data structure. A relation threshold may be set to identify a minimum number of identical variables between a first set of procedural metadata and a second set of procedural metadata. If the number of identical variables exceeds the relation threshold, the first node may be related to the second node.

At block 1110, a plurality of edges are generated to connect the new node to the first node and to the second node. In instances where more than one first node and/or more than one second node is identified, one or more additional edges can be generated. Each edge may correspond to a surgical action that results in a procedural state transitioning between states represented by the connected nodes. The discrete data points extracted from the surgical data can be used to identify a surgical action that is associated with transitioning from a first procedural state to a second procedural state. Also, procedural metadata associated with the new node, the first node, and the second node can be processed to identify surgical actions associated with transitioning from a first procedural state to a second procedural state.

At block 1112, the surgical data structure with the new node and the new edges can be updated by the local server, the remote server, and/or a computing device. For example, an array, relational database or other type of data structure may be updated to include an element corresponding to the new node and multiple edge elements corresponding to the generated edges. The updated surgical data structure can be transmitted to another network connected device.

It will be appreciated that the steps described in FIG. 11 may be performed during a surgical procedure (e.g., at a local surgery in an operating room or facility at which the procedure is being performed or at a remote server, such as a cloud server) or after the procedure using stored data collected during the procedure. For example, in one instance, surgical data is collected during a surgical procedure by devices located in an operating room, and subsequently a remote server may receive and process the surgical data. As another example, a local device may receive and process the surgery data during the procedure.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but can have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by (for example) hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

While the principles of the disclosure have been described above in connection with specific apparatuses and methods, it is to be clearly understood that this description is made only by way of example and not as limitation on the scope of the disclosure.

What is claimed is:

1. A method comprising:
    accessing, by one or more data processors executing instructions stored on a non-transitory computer readable storage medium, surgical data collected during performance of a surgical procedure, the surgical data comprising video data of the surgical procedure;
    determining, by the one or more data processors, a procedural state based on at least a portion of the surgical data;
    identifying, by the one or more data processors, a portion of the video data that is associated with the procedural state;
    associating, by the one or more data processors, temporal information of the portion of the video data with the procedural state;
    generating, by the one or more data processors, electronic data to be associated with the procedural state;
    continuing to determine, by the one or more data processors, one or more additional procedural states based on one or more other portions of the surgical data, identify one or more other portions of the video data associated with the one or more additional procedural states, associate temporal information of the one or more other portions of the video data with the one or more additional procedural states, and generate the electronic data to be associated with the one or more additional procedural states until the electronic data has been generated for all of the one or more additional procedural states of the surgical procedure;
    outputting the video data, wherein the electronic data is associated with the portion of the video data and the one or more other portions of the video data;
    parsing, by the one or more data processors, the video data to identify a predefined number of images associated with the procedural state and the one or more additional procedural states; and
    generating, by the one or more data processors, a document comprising the identified images and text based on the electronic data that describes one or more actions depicted in the identified images.

2. The method of claim 1, wherein the surgical data is received incrementally, and determining the procedural state comprises:
    aggregating the surgical data; and
    dividing the aggregated surgical data into separate chunks representative of distinct procedural states comprising the procedural state and the one or more additional procedural states.

3. The method of claim 2, wherein the separate chunks are identified based on a command indicative of a transition between procedural states in the surgical procedure.

4. The method of claim 1, wherein the electronic data comprises text that is overlaid or presented next to the portion of the video data.

5. The method of claim 1, wherein the electronic data comprises audio signal that is played back with the portion of the video data.

6. The method of claim 1, further comprising updating a patient record based on the electronic data.

7. A system comprising:
    one or more data processors; and
    a non-transitory computer readable storage medium containing instructions which when executed on the one or more data processors, cause the one or more data processors to perform actions including:
        accessing surgical data collected during performance of a surgical procedure, the surgical data comprising video data of the surgical procedure;
        determining a procedural state based on at least a portion of the surgical data;
        identifying a portion of the video data that is associated with the procedural state;
        associating temporal information of the portion of the video data with the procedural state;
        generating electronic data to be associated with the procedural state;
        continuing to determine one or more additional procedural states based on one or more other portions of the surgical data, identify one or more other portions of the video data associated with the one or more additional procedural states, associate temporal information of the one or more other portions of the video data with the one or more additional procedural states, and generate the electronic data to be associated with the one or more additional procedural states until the electronic data has been generated for all of the one or more additional procedural states of the surgical procedure;

outputting the video data, wherein the electronic data is associated with the portion of the video data and the one or more other portions of the video data;

parsing the video data to identify a predefined number of images associated with the procedural state and the one or more additional procedural states; and generating a document comprising the identified images and text based on the electronic data that describes one or more actions depicted in the identified images.

8. The system of claim 7, wherein the surgical data is received incrementally, and determining the procedural state comprises:

aggregating the surgical data; and dividing the aggregated surgical data into separate chunks representative of distinct procedural states comprising the procedural state and the one or more additional procedural states.

9. The system of claim 8, wherein the separate chunks are identified based on a command indicative of a transition between procedural states in the surgical procedure.

10. The system of claim 7, wherein the electronic data comprises text that is overlaid or presented next to the portion of the video data.

11. The system of claim 7, wherein the electronic data comprises audio signal that is played back with the portion of the video data.

12. The system of claim 11, wherein the one or more data processors update a patient record to include the video data.

13. A computer-program product tangibly embodied in a non-transitory machine-readable storage medium, including instructions configured to cause one or more data processors to perform actions comprising:

accessing surgical data collected during performance of a surgical procedure, the surgical data comprising video data of the surgical procedure;

determining a procedural state based on at least a portion of the surgical data;

identifying a portion of the video data that is associated with the procedural state;

associating temporal information of the portion of the video data with the procedural state;

generating electronic data to be associated with the procedural state;

continuing to determine one or more additional procedural states based on one or more other portions of the surgical data, identify one or more other portions of the video data associated with the one or more additional procedural states, associate temporal information of the one or more other portions of the video data with the one or more additional procedural states, and generate the electronic data to be associated with the one or more additional procedural states until the electronic data has been generated for all of the one or more additional procedural states of the surgical procedure;

outputting the video data, wherein the electronic data is associated with the portion of the video data and the one or more other portions of the video data;

parsing the video data to identify a predefined number of images associated with the procedural state and the one or more additional procedural states; and generating a document comprising the identified images and text based on the electronic data that describes one or more actions depicted in the identified images.

14. The computer-program product of claim 13, wherein the surgical data is received incrementally, and determining the procedural state comprises:

aggregating the surgical data; and dividing the aggregated surgical data into separate chunks representative of distinct procedural states comprising the procedural state and the one or more additional procedural states.

15. The computer-program product of claim 14, wherein the separate chunks are identified based on a command indicative of a transition between procedural states in the surgical procedure.

16. The computer-program product of claim 13, wherein the electronic data comprises text that is overlaid or presented next to the portion of the video data.

17. The computer-program product of claim 13, wherein the electronic data comprises audio signal that is played back with the portion of the video data.

* * * * *